(12) United States Patent
Abedin-Nasab

(10) Patent No.: US 10,603,122 B2
(45) Date of Patent: Mar. 31, 2020

(54) SURGICAL ROBOT

(71) Applicant: Rowan University, Glassboro, NJ (US)

(72) Inventor: Mohammad Abedin-Nasab, Glassboro, NJ (US)

(73) Assignee: Rowan University, Glassboro, NJ (US)

( * ) Notice: Subject to any disclaimer, the term of this patent is extended or adjusted under 35 U.S.C. 154(b) by 40 days.

(21) Appl. No.: 15/749,626

(22) PCT Filed: Feb. 17, 2017

(86) PCT No.: PCT/US2017/018393
§ 371 (c)(1),
(2) Date: Feb. 1, 2018

(87) PCT Pub. No.: WO2017/143204
PCT Pub. Date: Aug. 24, 2017

(65) Prior Publication Data
US 2018/0368928 A1    Dec. 27, 2018

Related U.S. Application Data

(60) Provisional application No. 62/296,212, filed on Feb. 17, 2016.

(51) Int. Cl.
*A61B 17/30* (2006.01)
*A61B 17/88* (2006.01)
(Continued)

(52) U.S. Cl.
CPC ........ *A61B 34/30* (2016.02); *A61B 17/00234* (2013.01); *A61B 17/62* (2013.01);
(Continued)

(58) Field of Classification Search
CPC ..................................................... A61B 34/30
See application file for complete search history.

(56) References Cited

U.S. PATENT DOCUMENTS

| 4,784,125 A | 11/1988 | Monticelli et al. |
| 6,368,330 B1 * | 4/2002 | Hynes .................... A61B 90/11 600/429 |

(Continued)

FOREIGN PATENT DOCUMENTS

| CN | 101178306 A | 5/2008 |
| CN | 102179807 A | 9/2011 |

(Continued)

OTHER PUBLICATIONS

Communication, Extended European Search Report, European Patent Application No. 17753933.5, dated Sep. 12, 2019.
International Search Report and Written Opinion, International Patent Application No. PCT/US2017/018393, dated Jul. 17, 2017.
(Continued)

*Primary Examiner* — Christian A Sevilla
(74) *Attorney, Agent, or Firm* — Saul Ewing Arnstein & Lehr LLP; Brian R. Landry; Domingos J. Silva

(57) ABSTRACT

A surgical robot includes a fixed frame and a moving frame, each having an open space in a center region and may be formed as a partially open ring. The robot also includes three leg structures connecting the fixed frame and the moving frame, and enabling the moving frame to move relative to the fixed frame. The robot also includes a stabilizer for holding an anatomical structure in the open space of each frame. Each leg structure may include a linear component coupled to the moving frame, a rotary component mounted to the fixed frame, and a connector connecting between the two. Each of the linear component and the rotary component may have a rotary actuator that can be controlled by a computer. The robot may be controllable by a computer to assist a reduction procedure of long bone fractures or pelvis surgery.

22 Claims, 16 Drawing Sheets

(51) Int. Cl.
  *A61B 34/30* (2016.01)
  *A61B 90/50* (2016.01)
  *A61B 17/62* (2006.01)
  *A61B 34/00* (2016.01)
  *A61B 17/00* (2006.01)
  *A61B 90/00* (2016.01)
  *A61B 90/57* (2016.01)
  *A61B 17/56* (2006.01)

(52) U.S. Cl.
  CPC .............. *A61B 17/88* (2013.01); *A61B 34/25* (2016.02); *A61B 34/76* (2016.02); *A61B 90/50* (2016.02); *A61B 2017/00398* (2013.01); *A61B 2017/564* (2013.01); *A61B 2034/304* (2016.02); *A61B 2090/064* (2016.02); *A61B 2090/376* (2016.02); *A61B 2090/378* (2016.02); *A61B 2090/571* (2016.02)

(56) References Cited

U.S. PATENT DOCUMENTS

| | | | |
|---|---|---|---|
| 8,333,766 B2* | 12/2012 | Edelhauser | A61B 17/62 606/55 |
| 2010/0087819 A1* | 4/2010 | Mullaney | A61B 17/62 606/56 |
| 2010/0234844 A1 | 9/2010 | Edelhauser et al. | |
| 2015/0112340 A1 | 4/2015 | Kahvecioglu | |

FOREIGN PATENT DOCUMENTS

| | | |
|---|---|---|
| WO | 2012102685 A1 | 8/2012 |
| WO | 2014201340 A1 | 12/2014 |

OTHER PUBLICATIONS

International Preliminary Report on Patentability, International Patent Application No. PCT/US2017/018393, dated Aug. 21, 2018.

* cited by examiner

SURGICAL ROBOT

RELATED APPLICATION

This application is a U.S. national stage application of International Application No. PCT/US2017/018393, filed Feb. 17, 2017, which claims the benefit of priority of U.S. Provisional Patent Application No. 62/296,212, filed Feb. 17, 2016, the entire disclosure of each of which are hereby incorporated herein by reference in its entirety.

BACKGROUND

This disclosure relates to robotic systems and in particular to robotic systems for treatment of bone fractures.

Lower limb fractures account for nearly a third of all fractures, and the ratio is still growing, due to the ageing of the population. A large number of lower limb fractures, that are very common in trauma centers, are those associated with long bones. The treatment of long bone fractures includes two main steps. First, the fracture is reduced, and then the bone fragments are fixed by external or internal fixation systems, e.g., plates and intramedullary nails. Due to its minimally invasive nature, intramedullary nailing technique is the treatment of choice of many surgeons for femoral and tibial shaft fractures.

However, accurate reduction of long bone fractures is difficult to achieve using the conventional surgical techniques. High radiation exposure, to both the patient and the operating team, and malalignment of the bony fragments frequently occur; the latter can dramatically affect the course of healing, leading to nonunion complications. Also, soft tissue damages, due to large manipulation forces and repeated reduction attempts, are common. As such, there is a need to develop systems that can effectively improve clinical outcomes in patients undergoing bone reduction surgery.

This document describes systems and methods to address the shortcomings in the art.

SUMMARY

The present invention is directed to robotic systems and method of using such systems to perform orthopedic surgeries, such as bone long bone reduction, pelvic surgery, joint reconstructions, foot and ankle surgery, and arthroscopy. At least one aspect of the present invention is directed to methods of performing a guided orthopedic surgery by attaching proximal fragments of a fractured bone to a fixed frame of a robot; attaching a distal fragment of the fractured bone to a moving frame of the robot; and align these fragments to a desired position for optimal patient outcome.

In some embodiments, a surgical robot may include a fixed frame and a moving frame. Each of the fixed frame and moving frame defines a respective plane, and includes an open space in a center region. Each frame may also be formed as a partially annular ring having an opening therein. The robot may also include three leg structures connecting the fixed frame and the moving frame, and configured to move the moving frame relative to the fixed frame. The robot may also include a stabilizer configured to hold an anatomical structure in the open space formed in the center region of each of the moving frame and the fixed frame.

The stabilizer may include at least one rod attached at varying locations along the fixed frame and extending from the fixed frame towards the open space formed in the center region thereof. The at least one rod associated with the fixed frame can be configured to be positioned to hold a first fragment of the anatomical structure in place relative to the fixed frame. Similarly, the stabilizer may also include at least one rod attached at varying locations along the moving frame and extending from the moving frame towards the open space formed in the center region thereof. The at least one rod associated with the moving frame can be configured to be positioned to hold a second fragment of the anatomical structure in place relative to the moving frame.

In some embodiments, each of the three leg structures may include a linear component that facilitates a sliding component to travel in a linear motion longitudinally along the leg structure, in which the sliding component is coupled to the moving frame at a mounting location. The linear component of each leg structure may also be coupled to a first actuator to move the sliding component longitudinally along the leg structure. The first actuator of each leg structure may be a rotary actuator. Each leg structure may also include a screw shaft coupled to the first actuator to transfer rotational motion from the first actuator to the linear motion of the sliding component. Further, each leg structure may also include a rotary component mounted to the fixed frame at a mounting location, and a connector connecting the linear component to the rotary component. The connector can be of a U-shape.

In some embodiments, the rotary component may include a shaft couplable to a shaft of a second rotary actuator to transfer rotation of the rotary actuator to the connector. The rotary component may include a shaft connector positioned to be coupled to the shaft of the rotary component and also to pivotally connect to the connector of each leg structure. The rotary component may also include a key positioned to lock the shaft connector to the shaft of the rotary component. Each of the first and second rotary actuators for each leg structure can be configured to rotate using a servo or stepper motor.

In some embodiments, the mounting locations at which the sliding components for the three leg structures are coupled to the moving frame can be equally spaced, and the mounting locations at which the rotary component for the three leg structures are mounted to the fixed frame can also be equally spaced. In some embodiments, the mounting locations can be adjustable along the partially annular ring of the moving frame and/or fixed frame. In some embodiments, the fixed frame may have an extended plate at each mounting location to enable a rotary component to be mounted thereon. Each extended plate may lie in the same plane formed by the fixed frame.

In some embodiments, the fixed frame can be movably mounted to a stand that is configured to support the robot. The robot may also include an attachment device for attaching an image capturing device to the robot, the image capturing device is capable of capture one or more images in real-time during a surgery. The image capturing device can be an ultrasound device, an x-ray scanner or a combination thereof. In some embodiments, the robot may have an additional leg structure similar to the structure of other leg structures described above. The additional leg structure may connect a first additional element attachable to the fixed frame and a second additional element attachable to the moving frame. Each additional element may be attached to and close the opening of the respective frame.

In some embodiments, a robotic system may include the surgical robot described above, a processing device in communication with the first and second rotary actuators of each leg structure, and computer software stored in a non-transitory computer-readable storage medium to control each of the actuators during a reduction procedure of long bone fractures or pelvic surgeries. In the robotic system, each of the moving frame and the fixed frame are formed as a partially annular ring having an opening therein, and the opening of the moving frame and the opening of the fixed frame can be positioned around the long bone to reach a position for the procedure.

In some embodiments, a method for controlling a robot for use in a reduction procedure of a long bone fracture or pelvis surgery may include the steps of: attaching a proximal fragment of a fractured bone to a fixed frame of a robot; attaching a distal fragment of the fractured bone to a moving frame of the robot; by a processing device, moving the moving frame of the robot to a desired position; by the processing device, rotating the moving frame to allow parallel alignment to a shaft of the proximal fragment; by the processing device, translating the moving frame in a plane transverse to an axis of the proximal fragment to enable the axis of the distal fragment to align with an axis of the proximal fragment; and by the processing device, moving the moving frame to a target pose for a fracture end of the distal fragment to align with an opposing fracture end of the proximal fragment. In some embodiments, the moving frame may move in 6 degree of freedom in relation to the fixed frame.

The various steps of the method may also include receiving a position instruction from a user, such as a user command via a graphical user interface. The method may further include receiving, using a processing device, the position instruction; generating, using the processing device, one or more control parameters for one or more actuators of the robot based on the received position instruction; transmitting, using the processing device, control signals representing the one or more parameters to the one or more actuators. The position instruction may include one or more of a x position, a y position, a z position, an alpha, a beta, a gamma, a delta Tm, a time interval, a step ratio, a delta Rot, and a sample time. The method may also include using an image-capturing device to capture in real-time one or more images during the procedure, where the one or more captured images include the fracture end of the distal fragment and the opposing fracture end of the proximal fragment, or a pelvis. In one embodiment, the method may include generating preoperative or intraoperative images at the surgical site and determining desired trajectories to align fractured fragments.

DETAILED DESCRIPTION

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

The term "leg" or "leg structure" as used herein refers to any structure that supports a moving frame on a fixed frame.

The term "frame" as used herein refers to any structure that comprises one or more fixed components and provides support for or positioning of a surgical instrument. The "frame" may form a two-dimensional (2D) plane or may be of any three-dimensional (3D) structure.

Figure 1:
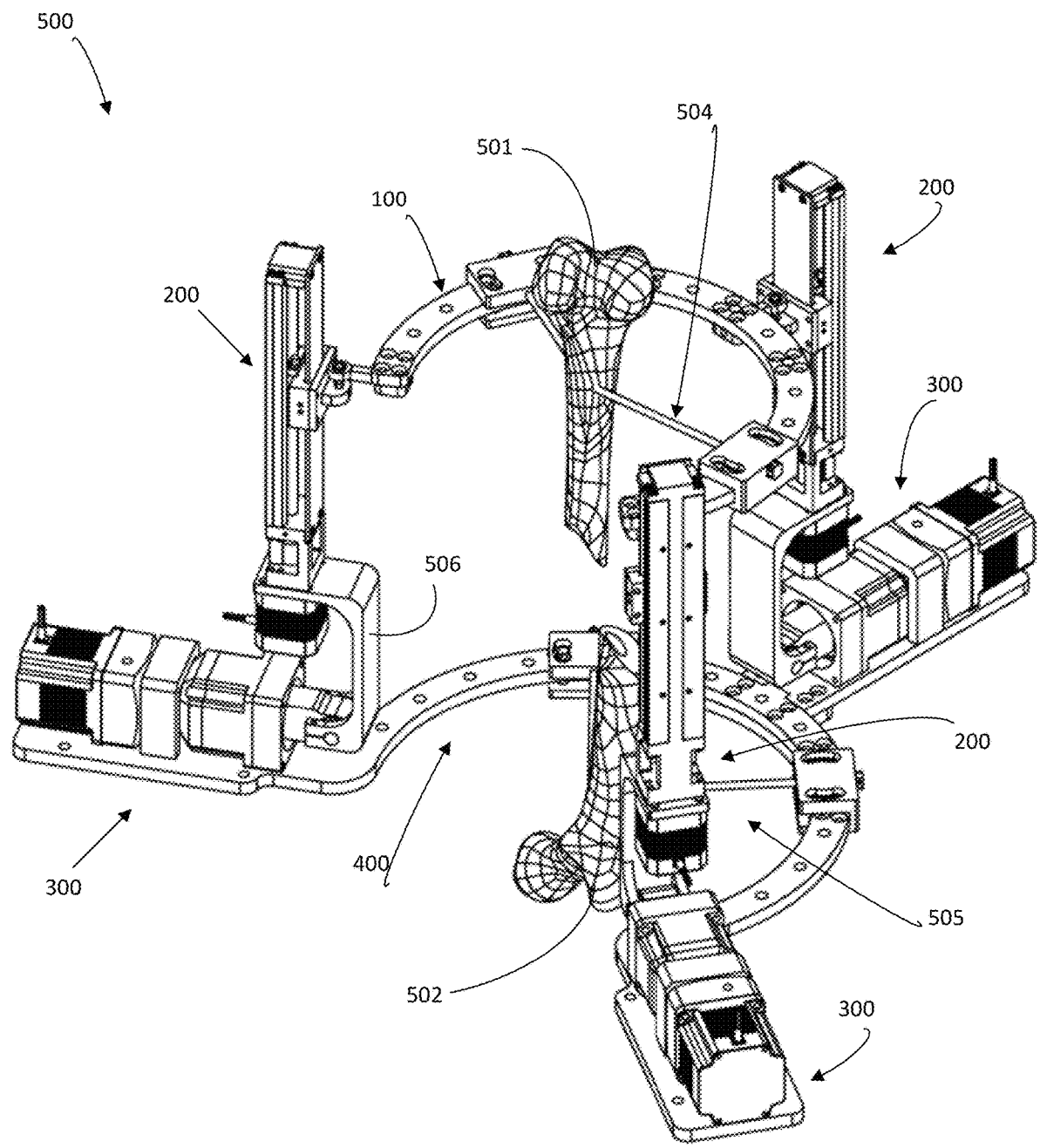
FIG. 1 depicts a perspective view of a robot according to some embodiments.

In FIG. 1, in some embodiments, a surgical robot 500 may include a fixed frame 400 and a moving frame 100, which will be described in detail later. The robot may also include multiple leg structures, which connect the fixed frame 400 and the moving frame 100. The leg structures may also be configured to enable the moving frame 100 to move relative to the fixed frame 400. In some embodiments, there may be three leg structures (FIG. 1). The robot 500 may also include a stabilizer 504, 505 that is configured to hold an anatomical structure 501, 502 during a reduction procedure for long bone fractures. In some embodiments, the stabilizer 504, 505 may also be configured to move a part of the anatomical structure to align with another part. For example, in the reduction procedure for long bone fractures, the stabilizer 504, 505 may be configured to align a distal fragment 501 of a long bone to a proximal fragment 502 of the long bone. In some embodiments, the stabilizer may contain a gripping member to grip, carry, hold or maintain the anatomical structure undergoing surgery.

In some embodiments, each leg structure may include a linear component 200, which facilitates a sliding component to travel in a linear motion longitudinally along the leg structure, and the sliding component may be coupled to the moving frame 100 at a mounting location. Additionally, and/or alternatively, each leg structure may include a gear box 300, which can be mounted to the fixed frame 400. In some embodiments, each leg structure may include a connector 506 to couple the linear component 200 with the gear box 300. The illustrated embodiments will enable the moving frame to move in 6-degrees-of-freedom.

Figure 2A:
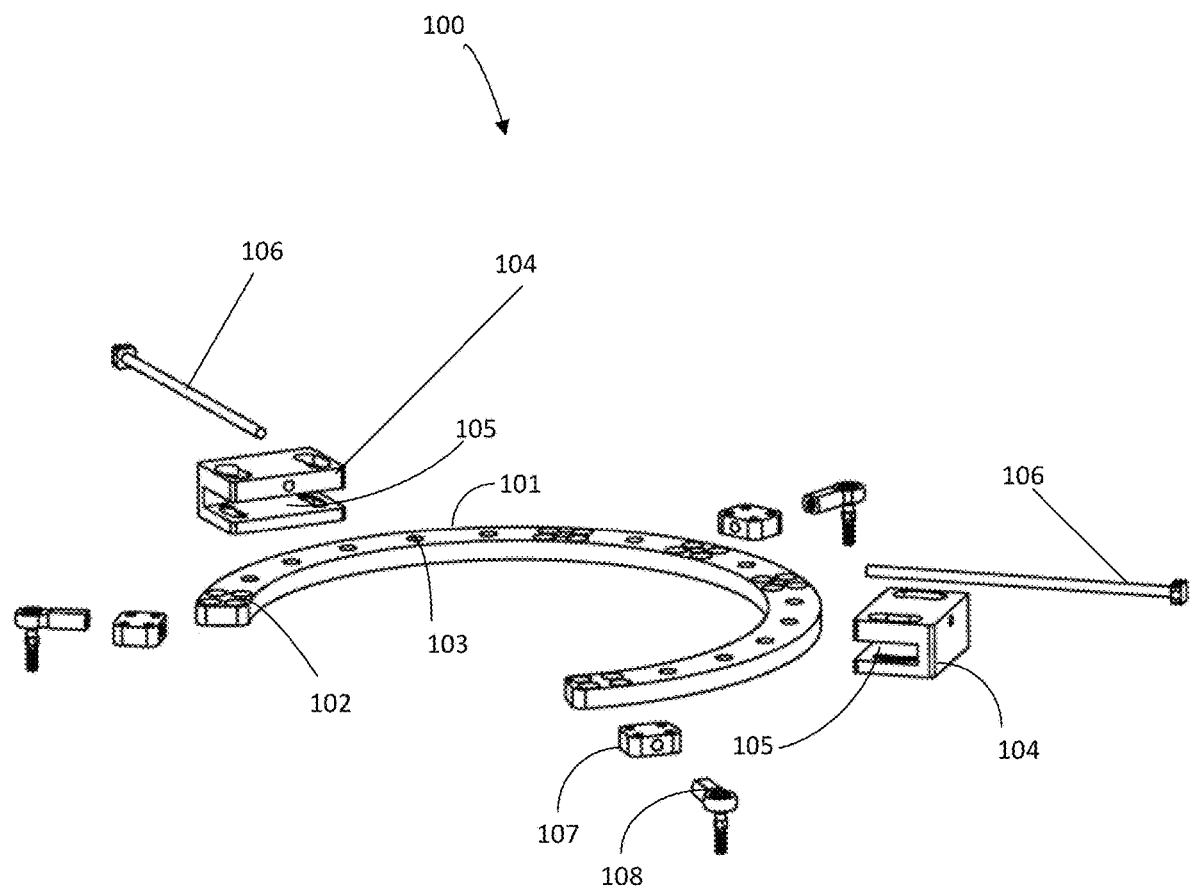
FIG. 2A is an exploded view of the moving frame of a robot according to some embodiments.

In FIG. 2A, the moving frame is further explained in detail. In some embodiments, the moving frame 100 may include an open space formed in the center region of the moving frame. The moving frame may be of any suitable shape. For example, the moving frame may form as a partially annular moving ring 101. In some embodiments, the moving frame can be at least a half-ring, can be a ¾ ring, with some variations, such as, for example, with ±25%. The moving frame can also be a full ring. The moving ring can also be adopted in other shapes such as square, partial square, ellipse, partial ellipse, oval or U-shape, partial oval, triangle, partial triangle, L-shape.

In some embodiments, the moving ring may be made of various suitable materials. For example, it can be metallic, aluminum, titanium alloys, stainless steel, hard plastic, polyolyphen or hard plastic alike, or anything capable of holding or supporting bone up to 400 Newton on an object without significant deflection (e.g. less than 5% deformity or bending or displaced more than 5%), or any material that can be sterilized and be used in a clean room environment. In some embodiments, the moving ring 101 may contain multiple holes of various types. For example, the hole 102 may be for fixing, adding or attaching other components to the moving ring; the hole 103 may be used for fastening the stabilizer to the frame. The thickness of the moving frame can range from 0.1 mm to 7.5 cm, preferably 0.5 mm to 2 cm, 10 mm to 1 cm, depending on the material used and the stiffness of the material.

In some embodiments, the stabilizer may include at least a grip, such as a rod 106 that is attached at varying locations along the moving frame and extending from the moving frame towards the open space formed in the center region of the moving frame, wherein the at least one rod is configured to be positioned to hold a bone fragment of the anatomical structure in place relative to the moving frame. The grip 106 may provide direct or indirect gripping of the anatomy under the surgery. It can pick up, hold, carry or guide a bone gripping mechanism.

In some embodiments, the moving frame may also include a fastener or bracket 104, which fastens the rod 106 to the moving frame. The fastener 104 may also be used to attach an instrument to the moving frame, such as an image sensor, a drug delivery component, a surgical instrument or other ancillary components required to perform the surgery. In some embodiments, the stabilizer rod 106 can be configured to secure a bone fragment in place relative to the moving ring. The stabilizer may be in contact with a bone fragment using simple screws, or clamped, mounted, or suctioned to the bone, forceps, modified scalpel, or it can be cuffs, braces to hold or connect to the bone or the soft tissue containing the bone, or can be other grips.

In some embodiments, the fastener 104 may contain one or two holes for attaching to the moving ring. It can be rotated to be aligned to the moving ring. It may be made of same material as moving ring. The fastener may also have a hole that allows passing through any grip, such as a rod 106 or pins, surgical needle, surgical instruments, lapraoscopic hands or device, drill, hollow cylinder to insert or guide other surgical instruments such as catherization tubes. The fastener 104 may also contain grooves 105 positioned to fit in the moving frame 101. The fastener 104 may also change orientation, and facilitate the rotation of the grip on the moving ring.

In some embodiments, the moving frame 101 may have one or more holes 102 for attaching a joint, e.g. a ball and socket joint for coupling to the linear component (200 in FIG. 1) of the leg structure. The moving platform may optionally have a fastener 107 for attaching the ball and socket joint to the moving ring 101. The fastener 107 can be screwed to the moving ring, welded, glued, or include a sliding component to facilitate flexibility of movement for ball and socket joint. To facilitate six-degrees-freedom of the moving frame, the coupling between the moving frame and the leg structure may further use a ball and socket joint 108 that provides or has three-degrees-of-freedom which connects the moving platform to the leg structure.

Figures 3A, 3B:
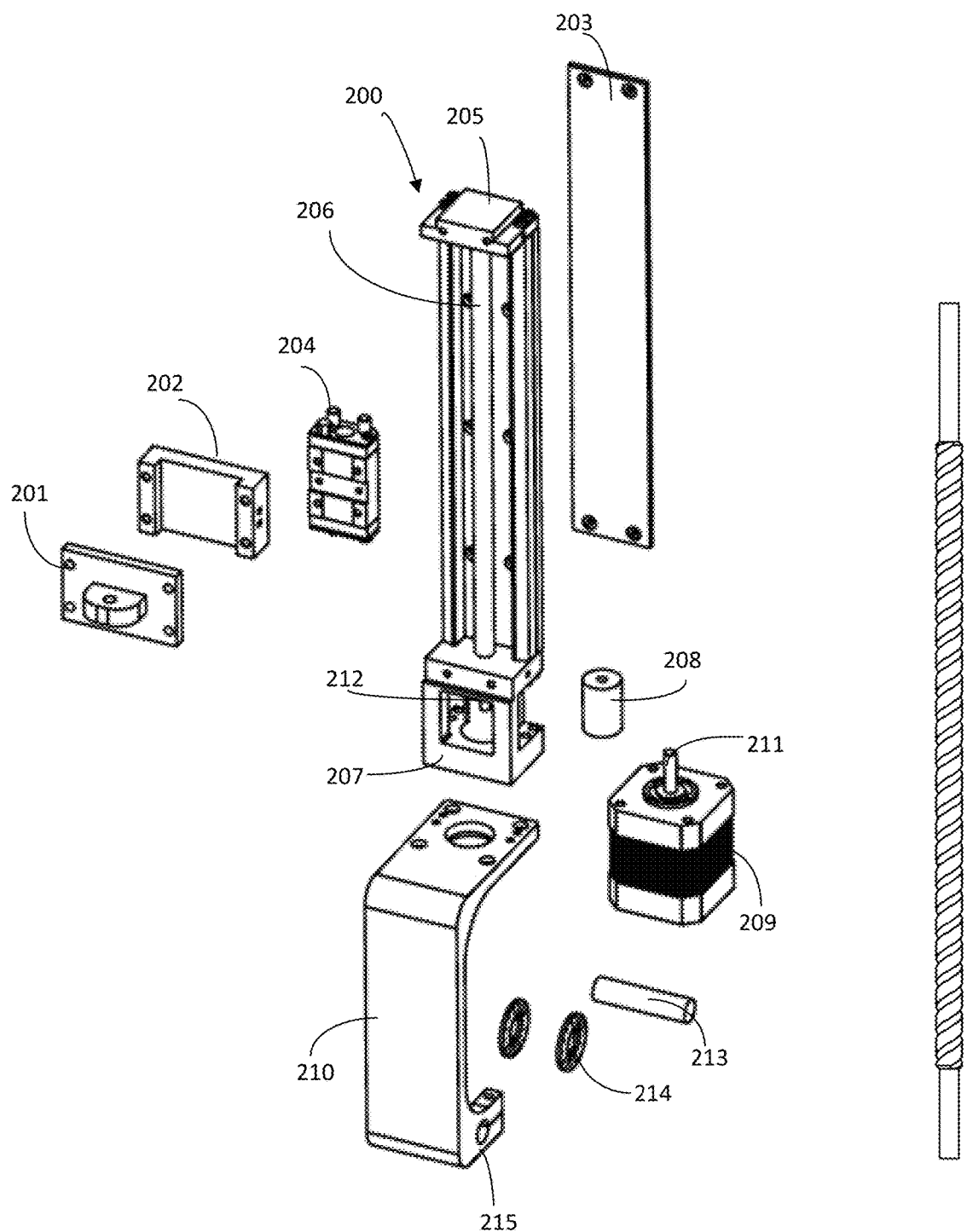
FIG. 3A is an exploded view of some components of the leg structure according to some embodiments.
FIG. 3B depicts an example of a screw shaft according to some embodiments.

In FIG. 3A, in some embodiments, the linear component 200 of the leg structure may have an upper housing 205. The linear component 200 may also have a connector 201 that facilitates the coupling of the leg structure to the moving frame by receiving the ball and socket joint of the moving frame (108 in FIG. 2A) into a hole thereon. In some embodiments, the linear component may be configured to move a sliding component, e.g. 204, longitudinally along the leg structure. In some embodiments, the linear component 200 may be configured to be coupled to an actuator 209 to provide one-degree freedom to the leg structure. The actuator can be of various types, e.g. a linear actuator or a rotary actuator. In some embodiments, the actuator can be a rotary actuator. The rotary actuator may use a servo or stepper motor. In some embodiments, the rotary actuator 209 can be an electric actuator motor. It may be controlled by computer software commands, or a processing device or a microcontroller, automatically or manually, hinged on the operator platform or surgeon console. The housing of the actuator can be made of the same material as indicated above, aluminum, steel, titanium, or any material that can be sterilized in clean room environment.

Each leg structure may also include a screw shaft 206 configured to be coupled to the actuator 209 and to transfer a rotational motion from the actuator to a linear motion of the sliding component 204. An exploded view of the screw shaft is also shown in FIG. 3B. The sliding component can be a nut on the screw that moves in a linear fashion longitudinally along the linear component. The linear component may also have a coupling housing 207 attached thereto from underneath the upper housing 205 and that allows coupling of the shaft of the rotary actuator 211 and the transmission of the rotation of the rotary actuator to the rotation of the shaft of the screw 206. The leg structure may also include a lower extremity 210, e.g. a connector, which facilitates the attachment of the rotary actuator 209 to the coupling housing 207 at one end. The leg structure may also be configured to couple to a rotary component such as a rotary gear box (300 in FIG. 1) at an opposing end, which will be explained later.

Alternatively, the coupling housing 207 may be positioned in the vicinity of the upper housing 200, for example, on top of the upper housing or below it, or behind the upper housing. The coupling housing 207 may include a coupler 208 positioned to fit between the lower part of the upper housing 212 and upper part of the shaft of the rotary actuator 211 to align the respective shafts and facilitate transmission of rotary force. The coupler 208 can be flexible coupling made of metal, aluminum, alloy or combination with plastic. It can be a closed, open or semi open housing.

In some embodiments, the upper housing 205 may be a nut screw assembly. It may have an optional cover 203 to close the screw and avoid dust accumulation inside the box. The sliding component 204 may be made of a screw shaft 206 and a nut, the nut itself may contain ball bearings to allow smooth movement of the nut on the screw shaft 206.

The upper housing 205 may be configured to hold the screw shaft 206. The screw shaft 206 may have a groove thereon longitudinally to allow nut 204 (which contains a ball for moving in the groove and the screw connector 202) to move up and down the screw in a linear fashion. The housing 205 itself may also include back wall, side walls, an upper ceiling or a lower base (now shown).

In some embodiments, the connector 201 may be used to attach or connect the moving frame to the leg structure, which may be the only point of attachment between the upper part of the leg structure and the moving frame. The connector 201 may contain a back plate which can be directly attached to the sliding nut 204 or indirectly through the middle connector 202 in cases where a cover is used. The connector 202 can be a U-shape connector that embraces the cover and allow movement of the connector 201 moveable up and down along the cover while being engaged with the nut and the screw shaft 206.

In some embodiments, the coupling housing 207 may include a coupler 208, upper part of the rotary shaft 211 and a lower part 212 that may extend from the screw shaft through the base of the upper housing 205 and through the ceiling of the coupling housing to meet within the coupling house space. In some embodiments, the lower extremity 210 may include a U-shaped and semi-U-shaped connector having three surfaces, an arm and two surfaces perpendicular to the arm to allow fastening of the lower extremities to other component of the robot. In some embodiments, the lower extremity may be a semi-U-shaped structural part that facilitates coupling of the upper housing to the rotary gear box system 300. In some embodiments, the coupling of the upper housing 205 and the rotary gear box may be directly through the coupling housing 207 without using a connector. In some embodiments, the connector 210 may have receptive holes 215 that receive a rod pin 213 to facilitate connecting to the rotary gear box system 300, which will be further explained with reference to FIG. 4.

Figure 4:
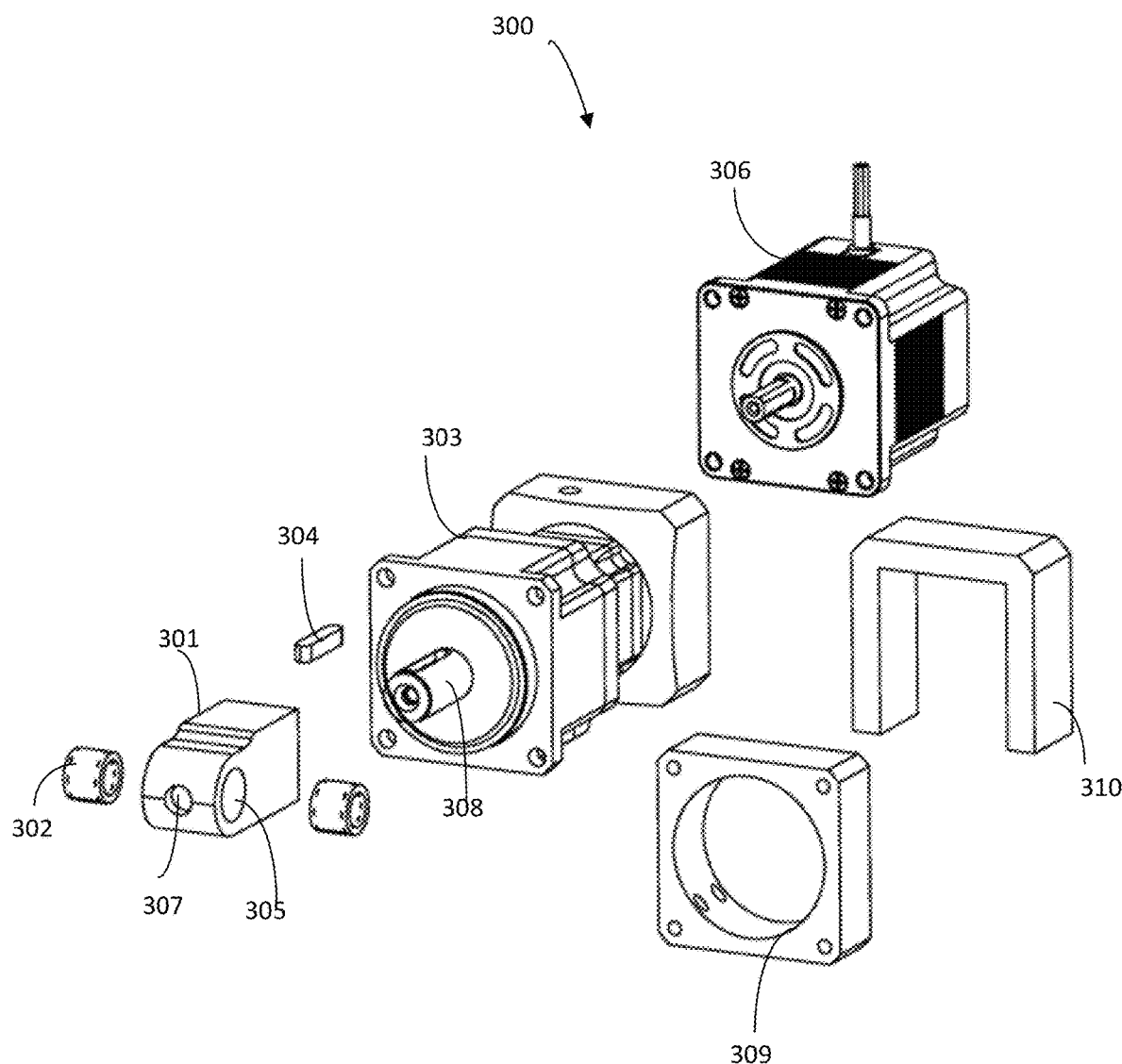
FIG. 4 is an exploded view of some components of a gear box according to some embodiments.

With reference to FIG. 3 and FIG. 4, in some embodiments, the rotary gear box system 300 may be mounted to the fixed frame at a mounting location, such as shown in FIG. 1. The rotary gear box system may include a shaft couplable to a shaft of a second rotary actuator and configured to transfer rotation of the rotary actuator to the connector 210. The second rotary actuator may use a servo or stepper motor. The rotary gear box system 300 may also include a shaft connector 301 positioned to be coupled to the shaft of the rotary gear box 308 and also to pivotally connect to the connector of each leg structure, e.g. connector 210. The rotary gear box system 300 may also include a key 304 positioned to lock the shaft connector 301 to the shaft of the rotary gear box 308. In some embodiments, the rod 213 may pass through the holes 215 of the lower extremities and a hollow space 305 of the shaft connector 301, where the hollow space 305 is aligned in between the receptive holes 215, coupling the lower extremities to a rotary gear box 303 optionally in its respective housing.

Optionally, the coupling between the rotary gear box system 300 and the linear component 200 (or connector 210) may use thrust lower bearing 214 to smoothen the connection and minimize the friction between the connector 211 and the outer surface of the gear box shaft connector 301. The shaft connector 301 can also optionally contain roller bearings 302 inside its hollow space 305, which allows smooth rotating of the rod 213 when inside the connector 301. The shaft connector 301 can optionally contain hollow pathway 307 to allow a screw to be fastened to the gearbox shaft of 308 and at the same time permit a gearbox shaft key 304 to lock into the connector with little or no axial movement or compression.

In some embodiments, the rotary gear box system 300 may also have a gear box housing 303 and a rotary actuator 306. The gear box housing 303 can be one- or two-stage gear box or has more than two stages, to enhance the torque generated by the rotary actuator, reduce the speed of the rotary actuator and further transmit the force and rotation of the rotatory actuator 306 to the linear component 200 through the shaft connector 301. The rotary gear box system 300 may also include connectors 309, 310 configured to mount the rotary gear box assembly to the fixed frame, which will be further explained.

Figure 2B:
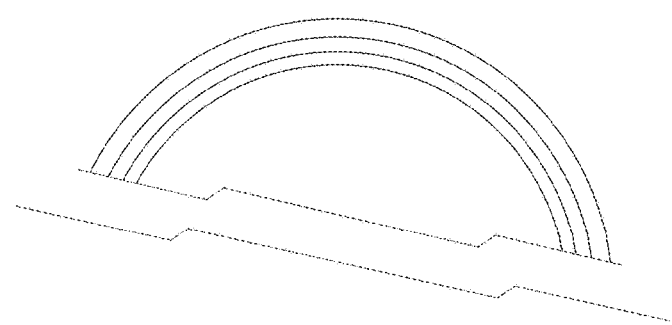
FIG. 2B depicts an example of a moving frame with sliding tracks for adjusting the location of leg structures according to some embodiments.
Figure 5:
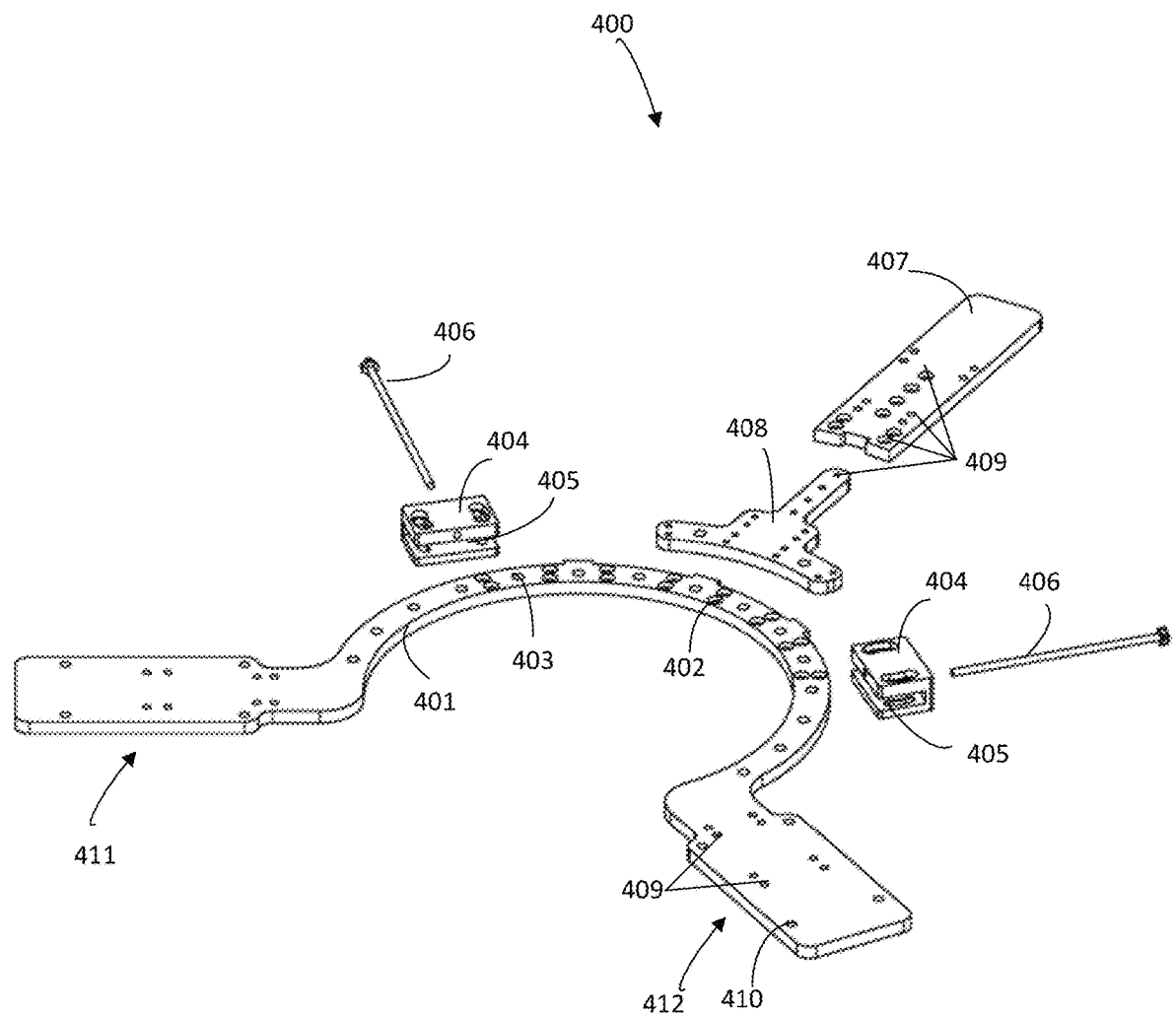
FIG. 5 is an exploded view of the fixed frame of a robot according to some embodiments.

In FIG. 5, the fixed frame is explained in detail. In some embodiments, the fixed frame may have similar structure of the moving frame (as shown in FIG. 2A). With reference to FIGS. 2 and 5 together, the mounting locations at which the sliding components for the three leg structures are coupled to the moving frame may be equally spaced or spaced variably. The mounting locations at which the rotary gear box systems for the three leg structures are mounted to the fixed frame may also be equally spaced or spaced variably. For example, the mounting location at which the sliding component for a middle leg structure of the three leg structures is coupled to the moving frame may be adjustable along the partially annular ring of the moving frame, so that the middle leg structure can slide towards the other two proximal legs within the movable ring. In some embodiments, the adjustment of the leg structures along the frames can be possible by using one or more mounting holes 102. In other embodiments, the adjustment can be possible by using a frame that has one or more tracks along the arc of the ring (FIG. 2B) that facilitate a movement of a slider on the frame.

Similarly, the mounting location at which the rotary gear box system for a middle leg structure of the three leg structures is mounted to the fixed frame may also be adjustable along the partially annular ring of the fixed frame. Alternatively, and/or additionally, the location of any of the other leg structures may also be adjustable. In some embodiments, the body of the fixed and movable rings may include a railing to facilitate movement of the leg structure(s). Alternatively, at least one actuator may be attached to the frames or the middle legs to allow automatic movement or sliding of the middle leg structure thought out the frames.

In FIG. 5, in some embodiments, the fixed frame 400 may include an open space formed in the center region of the fixed frame. The fixed frame may be of any suitable shape. For example, the fixed frame may form as a partially annular fixed ring 401. In some embodiments, the fixed frame can be at least a half-ring, can be a ¾ ring, with some variations, such as, for example, with ±25%. The fixed frame can also be a full ring. The fixed ring can also be adopted in other shapes such as square, partial square, ellipse, partial ellipse, oval or U-shape, partial oval, triangle, partial triangle, L-shape.

In some embodiments, the fixed ring may be made of various suitable materials. For example, it can be metallic, aluminum, titanium alloys, stainless steel, hard plastic, polyolyphen or hard plastic alike, or anything capable of holding or supporting bone up to 400 Newton on an object without significant deflection (e.g. less than 5% deformity or bending or displaced more than 5%), or any material that can be sterilized and be used in a clean room environment. In some embodiments, the fixed ring 401 may contain multiple holes of various types. For example, the holes 402 may be for mounting a rotary gear box system to the fixed ring; the holes 403 may be used for fastening the stabilizer to the frame or adding or attaching other components to the fixed ring. The thickness of the fixed frame can range from 0.1 mm to 7.5 cm, preferably 0.5 mm to 2 cm, 10 mm to 1 cm, depending on the material used and the stiffness of the material.

In some embodiments, the stabilizer may include at least a grip, such as a rod 406 that is attached at varying locations along the fixed frame and extending from the fixed frame towards the open space formed in the center region of the fixed frame, wherein the at least one rod is configured to be positioned to hold a bone fragment of the anatomical structure in place relative to the fixed frame. The grip 406 may provide direct or indirect gripping of the anatomy under the surgery. It can pick up, hold, carry or guide a bone gripping mechanism.

In some embodiments, the fixed frame may also include a fastener or bracket 404, which fastens the rod 406 to the fixed frame. The fastener 404 may also be used to attach an instrument to the fixed frame, such as an image sensor, a drug delivery component, a surgical instrument or other ancillary components required to perform the surgery. In some embodiments, the stabilizer rod 406 can be configured to secure a bone fragment in place relative to the fixed ring. The stabilizer may be in contact with a bone fragment using simple screws, or clamped, mounted, or suctioned to the bone, or it can be cuffs, braces to hold or connect to the bone or the soft tissue containing the bone, or can be other grips.

In some embodiments, the fastener 404 may contain one or two holes for attaching to the fixed ring. It can be rotated to be aligned to the fixed ring. It may be made of same material as fixed ring. The fastener may also have a hole that allows passing through any grip, such as a rod 406 or a pin, a surgical needle, surgical instruments, laprascopic hands or device, drill, hollow cylinder to insert or guide other surgical instruments such as catherization tubes. The fastener 404 may also contain grooves 405 positioned to fit in the fixed frame 401. The fastener 404 may also change orientation, and facilitate the rotation of the grip on the fixed ring.

In some embodiments, the fixed frame 401 may have one or more holes 402 for attaching a bone grip, such as a fastener 404 to the fixed ring 401 via holes 403, or fixing, adding or attaching other components to the fixed ring 401 via holes 402. In some embodiments, the holes 403 can be used for fixing or attaching image sensors or drug delivery components, surgical instrument or other ancillary components required to perform the surgery.

Returning to FIG. 5, in some embodiments, the fixed frame 400 may include an extended plate at each mounting location, wherein each extended plate is configured to enable a rotary gear box system to be mounted thereon. In some embodiments, each extended plate may lie in the same plane as that formed by the fixed frame, or the fixed ring 401. In some embodiments, a middle base plate for mounting a middle rotary gear box and actuator may be a single or multiple plate structure 407, 408, either directly or indirectly connected to the fixed ring through holes 402, which may be a single or double adjacent holes. The middle base plate(s) may contain a plurality of holes 409 to allow mounting of the rotary gear box system to the fixed ring.

In some embodiments, an open fixed ring 401 can contain a flat surface 411, 412 proximate to an end of the open fixed ring to allow resting of the rotary gear box system (the rotary gear box—actuator assembly) of the leg structures. These plates may contain various sets of holes. For example, the plates may include holes 409 used to mount the rotary gear box system to the surface of the plate. The plates may also include holes 410 used to connect the robot to a movable stand which will be explained hereinbelow.

Figure 6:
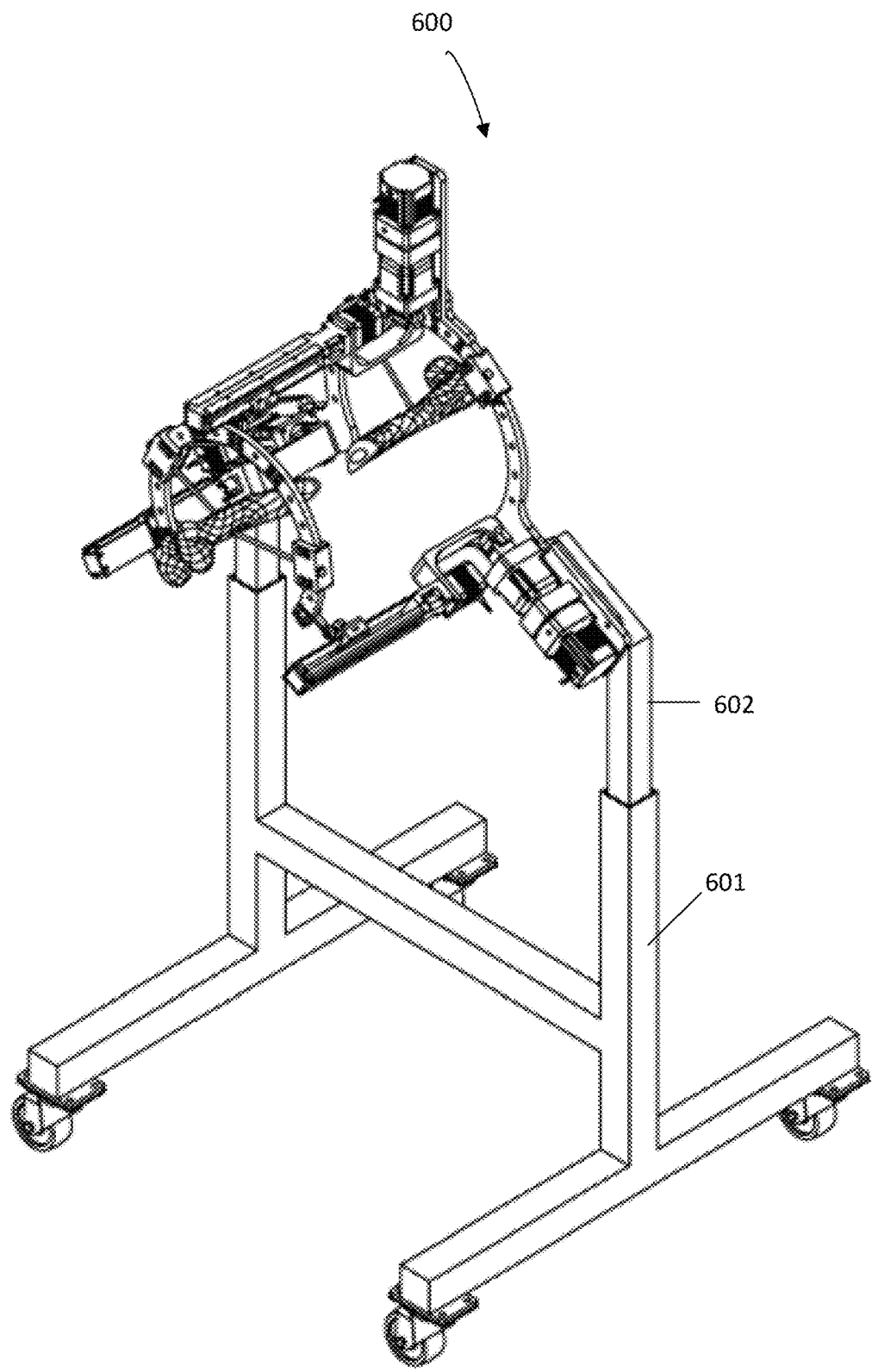
FIG. 6 depicts a perspective view of a robot attached to a movable stand according to some embodiments.
Figure 7:
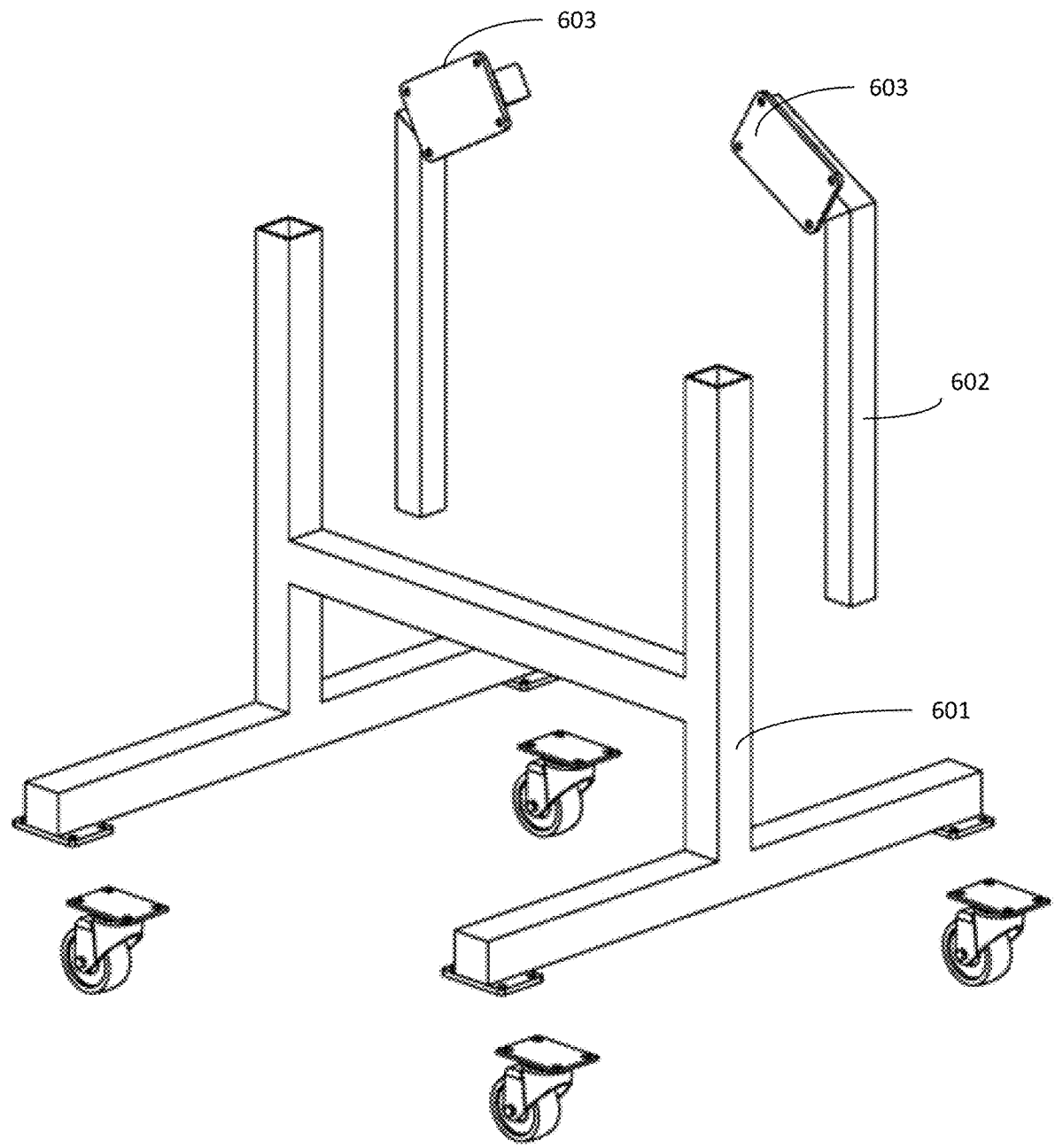
FIG. 7 depicts an exploded view of the stand of embodiments in FIG. 6.

In FIG. 6 and FIG. 7, a robotic system for a reduction procedure of large bone fractures may include the robot as described above, and additionally a stand 601. In some embodiments, the fixed frame is movably mounted to a stand that is configured to support the robot and enable the robot to be moved freely to a position for a reduction procedure of a long bone fracture. In some embodiments, the stand 600 may include a movable base 601 optionally containing locking wheels and an upper extension 602 containing one or more surfaces 603 that allow the mounting of one or more leg structures, e.g. 411, 412 (in FIG. 5) of the robot thereto.

In some embodiments, the system provides generating preoperative or intraoperative images at the surgical site and determining desired trajectories to align fractured fragments. As such, the robot further comprises an attachment device (now shown) configured for attaching an image capturing device to the robot, wherein the image capturing device is capable of being positioned to capture one or more images of the long bone fracture in real-time during the reduction procedure. In some embodiments, the image capturing device may be an x-ray scanner, a camera or other ultrasound imaging devices in mobile or stationary form. In other embodiments, the robot may have additional sensor attachments such as force sensors, position sensors, tracking sensor, vision tracking sensor, infrared sensor or the like to regulate respective parameters during the surgery such as haptic feedback trough the work of the surgeon.

Figure 8:
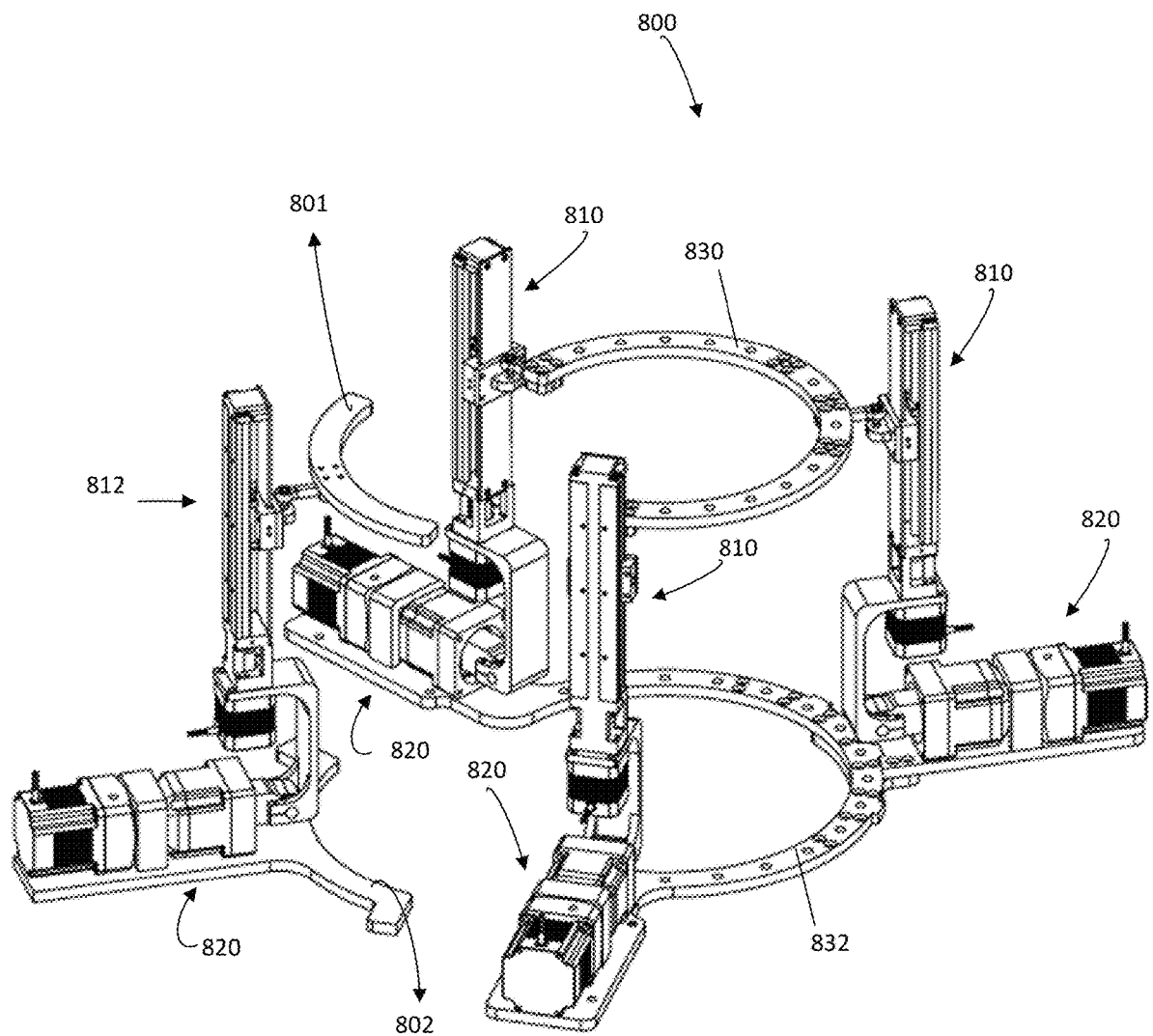
FIG. 8 depicts a perspective view of a robot with an additional leg structure according to some embodiments.
Figure 9:
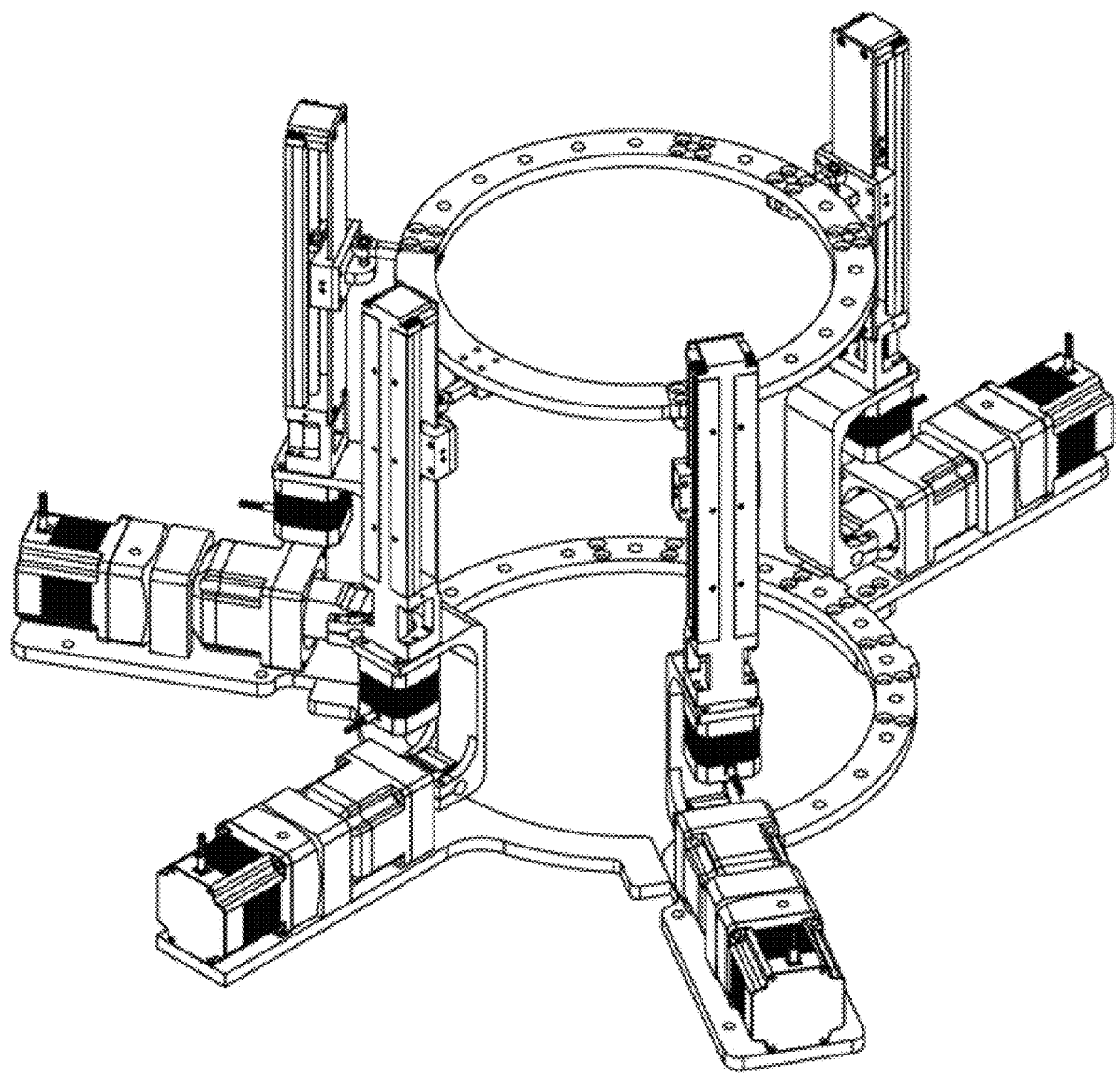
FIG. 9 depicts a perspective view of a robot with an additional leg structure according to some embodiments.

As shown in FIG. 8 and FIG. 9, the robot 800 may optionally contain an additional removable leg structure. In some embodiments, the robot 800 may include a first additional element attachable to the fixed frame 832 to close the opening of the fixed frame. The robot 800 may also include a second additional element attachable to the moving frame 830 to close the opening of the moving frame. The robot 800 may also include an additional leg structure 812 that may be of similar structure of other leg structures 810. The additional leg structure 812 may also be coupled to the moving frame 830 and mounted to the fixed frame 832 in a similar manner as other leg structures.

In some embodiments, the additional leg 812 may include a linear component that is couplable to an actuator to facilitate a sliding component to travel in a linear motion longitudinally along the additional leg structure, wherein the sliding component is mounted to the second additional element at a mounting location. The additional leg structure may also include a screw shaft configured to be coupled to the first actuator and to transfer rotation of the first actuator to the linear motion of the sliding component, a rotary gear box system mounted to the first additional element, and a connector connecting the linear component to the rotary gear box. The rotary gear box system of the additional leg structure may include a shaft couplable to a shaft of an additional rotary actuator and configured to transfer rotation of the rotary actuator to the connector. The additional leg structure may also include a shaft connector positioned to be coupled to the shaft of the rotary gear box and also pivotally connect to the connector of the additional leg structure.

The robot described in various illustrated embodiments in FIGS. 1-9 may be controlled by one or more processing devices in a robotic system that will allow the moving frame to move in six-degrees-of-freedom with precision in a reduction procedure for large bone fractures or pelvic surgeries. In some embodiments, the system may include the above described robot, and additionally include a processing device installable on the robot or remotely, and computer-readable storage medium or memory that contain programming instructions configured to cause the processing device to control each of the actuators during a reduction procedure of a long bone fracture or pelvic surgeries. In a computer assisted procedure, the robot may be movably mounted to a stand that is configured to support the robot and enable the robot to move freely to suitable position during a surgery, such as the reduction procedure of the long bone fracture or pelvic surgeries.

In some embodiments, the robotic system may further include an image capturing device positioned to capture one or more images of the surgical area, such as the long bone fracture or the pelvis, in real-time during the procedure. The image capturing device may be an x-ray scanner, a camera, other ultrasound, CT or MRI imaging devices to facilitate a guided orthopedic environment by generating preoperative or intraoperative images at the surgical site and determining desired trajectories to align fractured fragments.

In some embodiments, the precision control of the movement of the platform is further explained. Each of the actuators of the robot described in this document may require one or more control parameters in order to operate. The robotic system may be configured to receive the control parameters from a microprocessor or a processing device. The microprocessor may be configured to receive trajectory position instructions, convert the position instructions to one or more actuator control parameters and send the one or more control parameters to the one or more actuators via electrical signals. In some embodiments, the microprocessor may implement computer-readable program instructions (e.g. C, C++, Matlab, or any other computer languages) to convert desired trajectory position instructions to actuator control parameters.

Figure 10:
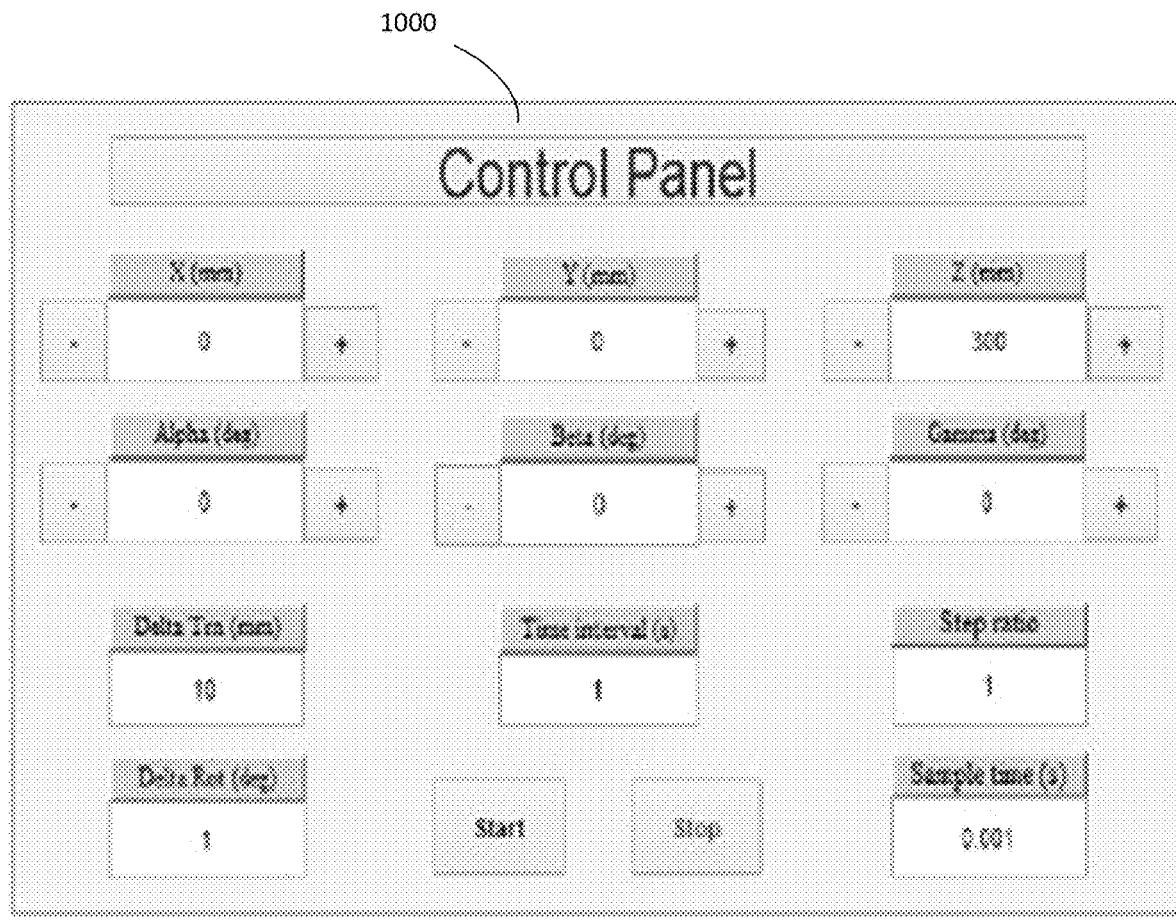
FIG. 10 depicts an example of a control panel as part of a user interface.

As shown in FIG. 10, in some embodiments, the robotic system can be controlled from a user (surgeon) manually or autonomously by receiving the position instruction in various ways. For example, the system may receive position instruction from a user via a control panel 1000, such as a touch screen control panel. Alternatively and/or additionally, the system may receive a command from a 6-DOF joystick that is connected to the system and operated by the user. The trajectory position instruction may include a multitude of values, such as x, y, z positions, alpha, beta, theta angles, steps and time intervals etc., Translational and rotational increments can be adjusted by "Delta Trn" and "Delta Rot" buttons, respectively. For instance, "Delta Trn" may range from 1 to 10 (mm), while "Delta Rot" may range from 0.1 to 1 (deg). "Sample time" ranges between 0.001 and 0.01 (s), and "Time interval" from 1 to 10 (s). "Step ratio" is dependent to the driver adjustments and may range from 1 to 250. The actuator control parameters may include the values for displacements and rotations of each actuator.

Figure 11:
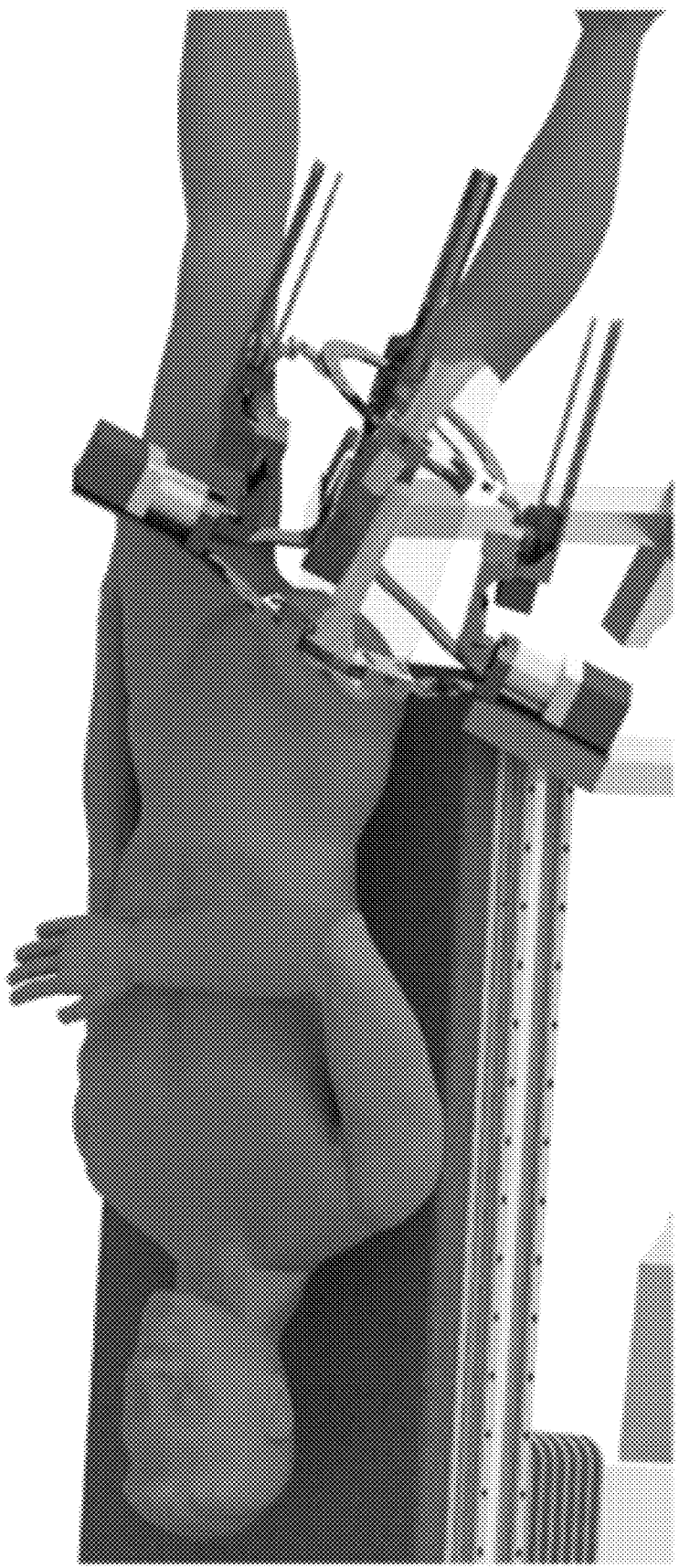
FIG. 11 depicts an example of a robotic system for use in a reduction procedure for large bone fractures.

In some embodiments, in the robotic system that is to be used for a reduction procedure of large bone fractures, as shown in FIG. 11, the robotic system may have a circular fixed and moving frames, with g (radius of the fixed ring) =15.6 (cm) and h (radius of the moving ring)=15.3 (cm), respectively. Each of the three leg structures may be equipped with a rotary actuator located on the fixed frame. This rotary actuator may include a 260 Watt stepper motor with a nominal torque of 0.83 N·m followed by a 10:1 low-ratio Apex gearbox, with a low clearance of 0.13°, such as the motor made by Autonics, to enlarge the shaft torque. The rotary gear box shaft may be connected to the lower part of the linear component of the leg structure using a revolute joint. The revolute joint may be made of a miniature needle bearing. Linear actuation at each leg structure may be provided using a ball screw system. The linear actuation may be powered by an 80 Watt stepper motor with a nominal torque of 0.24 N·m to provide sufficient torques, such as the stepper motor made by Autonics. The system may also include a spherical joint to connect the linear component or upper housing of the leg structure to the moving frame. The total mass of each of the three leg structure may be about 1.76 (kg) and that of the moving frame may be about 0.68 (kg). A graphical user interface, such as shown in FIG. 10, may also be included in the system to assist the user to perform the reduction procedure.

In at least some embodiments one of ordinary skill in the art may input suitable parameters to maximize clinical outcome based on population data. Such parameters may include x, y, and z as translational movements; alpha, beta, and gamma as rotational movements; translational resolution (a Delta Trn); rotational resolution (a Delta Rot); a time interval to reach to a target point; a Step ratio to signify the precision of the movement of the moving ring; and a Sample time of controlling signals from the computer to actuator. The control panel may further contain a start and stop button to regulate the movements and/or interrupt the movements in an emergency. As such, population data may be employed to designate the rotational workspace with dimensionless parameters.

In at least one aspect, method for controlling a robot is described during an orthopedic bone surgery. In some embodiments, a method of treating a single or complex long bone structure is described including the steps of: (a) attaching a proximal fragment of a fractured bone to a fixed frame of a robot; (b) attaching a distal fragment of the fractured bone to a moving frame of the robot; (c) by a processing device, moving the moving frame of the robot to a desired position, (d) by the processing device, rotating the moving frame to allow parallel alignment to a shaft of the proximal fragment, (e) by the processing device, translating the moving frame in a plane transverse to an axis of the proximal fragment to enable the axis of the distal fragment to align with an axis of the proximal fragment; and optionally (f) by the processing device, moving the moving frame to a target pose for a fracture end of the distal fragment to align with an opposing fracture end of the proximal fragment.

Figure 12:
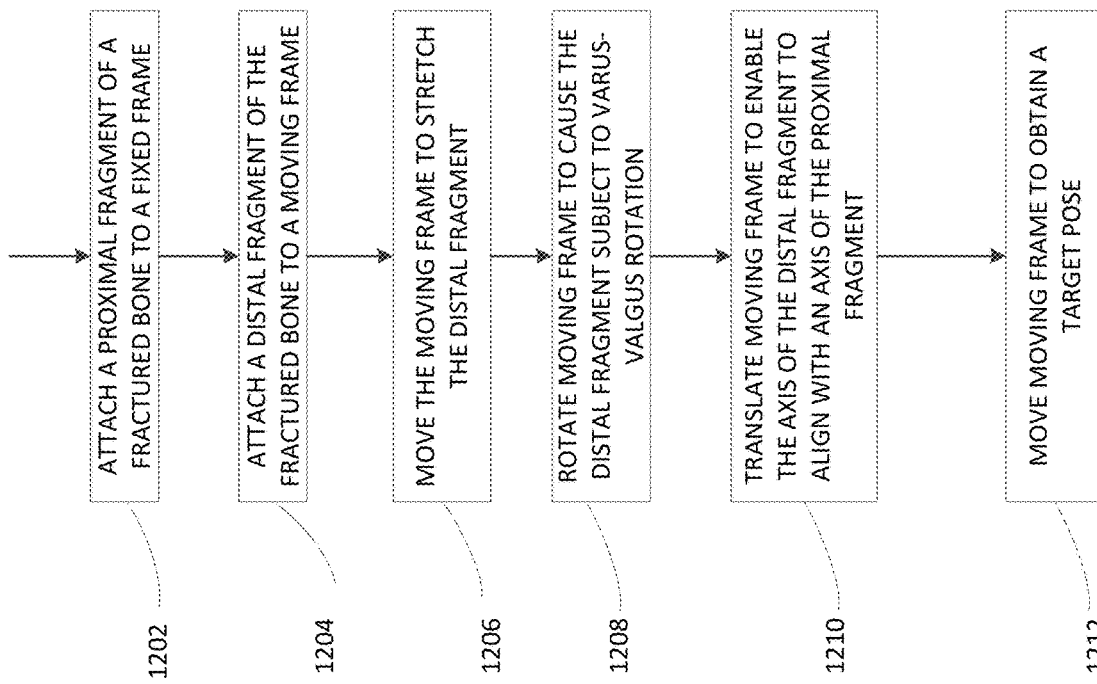
FIG. 12 shows a diagram of a process for controlling a robotic system according to some embodiments.

With reference to FIG. 12, in some embodiments, a method may be implemented using the various illustrated embodiments in FIG. 1-11 for a reduction procedure of large bone fractures. The method may include attaching a proximal fragment of a fractured bone to a fixed frame of a robot 1202, attaching a distal fragment of the fractured bone to a moving frame of the robot 1204. The method may additionally use a computer to control the robotic system. In some embodiments, the method may include moving the moving frame of the robot to stretch the distal fragment 1206 so that the distal fragment is separated from the proximal fragment. The method may also include rotating the moving frame to cause the distal fragment subject to varus-valgus rotation 1208 so that a shaft of the distal fragment lies parallel to a shaft of the proximal fragment. The method may further include translating the moving frame in a plane transverse to an axis of the proximal fragment to enable the axis of the distal fragment to align with an axis of the proximal fragment 1210, and moving the moving frame to shorten the distal fragment to obtain a target pose for a fracture end of the distal fragment to align with an opposing fracture end of the proximal fragment 1212.

In some embodiments, the steps of moving, rotating, translating and moving the moving frame may include receiving a position instruction from a user, e.g. via a graphical user interface. The method may additionally include using the computer to generate one or more control parameters for one or more actuators of the robot based on the received position instruction, and to operate the one or more actuators based on the one or more control parameters. Alternatively, and/or additionally, the method for performing the reduction procedure may also include using an image capturing device to capture in real-time one or more images during the surgery such as the reduction procedure, wherein the one or more captured images include the fracture end of the distal fragment and the opposing fracture end of the proximal fragment.

The various illustrated embodiments are advantageous over conventional surgical robots, such as the Stewart mechanism that has six legs with passive universal joints. The illustrated embodiments that have three or four leg structures are particularly suitable for computer assisted long-bone fracture reduction procedure in that the reduced number of legs make the robotic system lighter, since the rotary actuators are resting on the fixed frame, which allows for higher accelerations to be available due to smaller inertial effects. The leg structures in the illustrated system are also configured non-symmetrically on a semicircle on the base and moving platforms. This frontally wide open architecture, enables the mechanism to embrace and manipulate column-shape objects. The applications of such mechanism are versatile, from fracture reduction of long bones in surgical robotics to column climber robots in industrial robotics.

A kinematic analysis has been conducted on the illustrated embodiments above to verify the applicability of the system to the fracture reduction of long bones. As shown in the FIG. 13, coordinate $C_i(A_i, x_i, y_i, z_i)$ is attached to the base platform with its $x_i$ axis aligned with the rotary actuator in the $x_i$ direction, and its $z_i$ axis perpendicular to the fixed platform. $x_i$ is rotated by $\gamma_i$ from the X direction of fixed platform coordinate $A(O, X, Y, Z)$. The rotary actuators are located at the positions $A_i$ (for i=1, 2, 3, 4) on the base platform and each shaft is connected to the lower part of the linear actuators through a universal joint. The upper parts of linear actuators are connected to the moving platform, $B_i$ points, through spherical joints.

Figure 13:
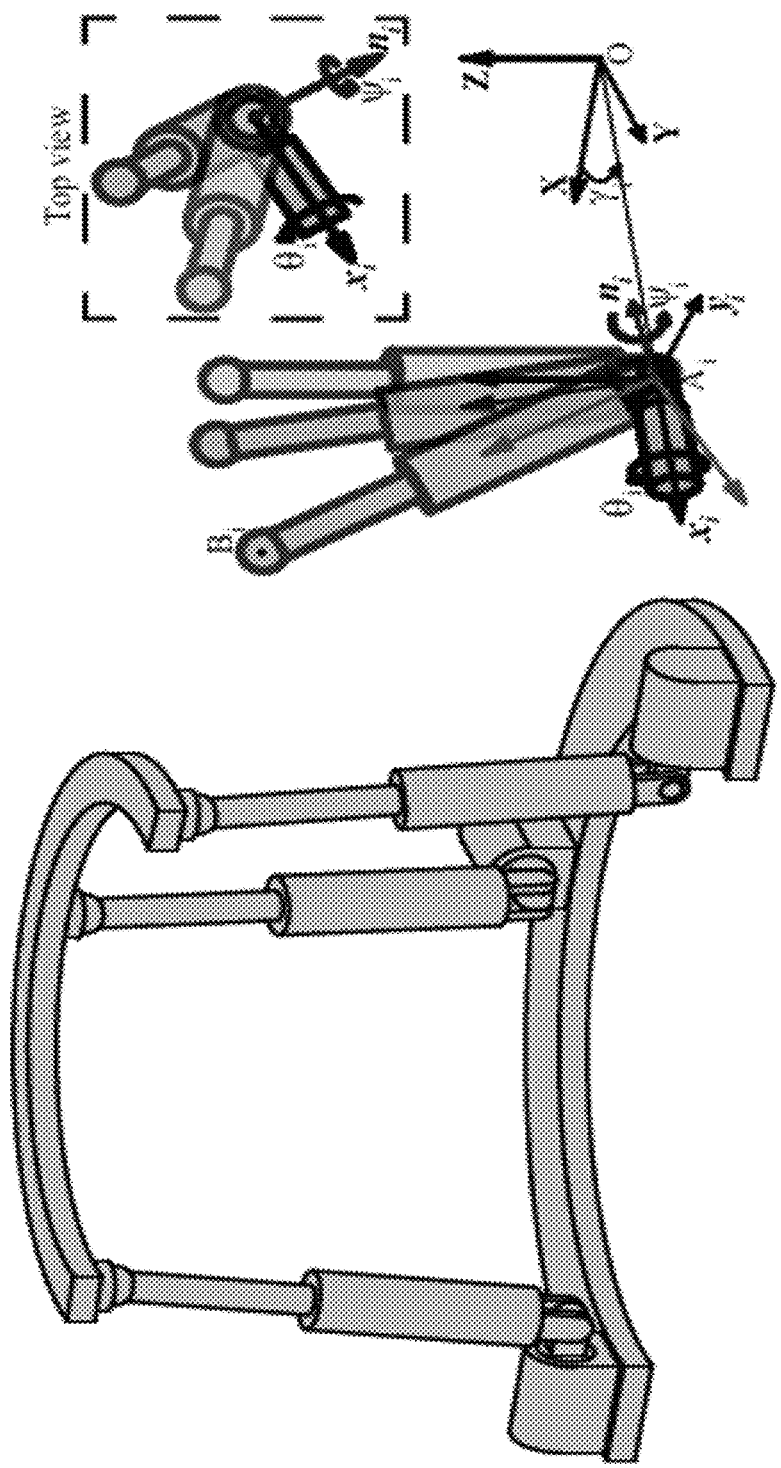
FIG. 13 shows a schematic 6-degree-of-freedom robot with three legs and coordinates for an evaluation.

Cartesian coordinates $A(O, x, y, z)$ and $B(P, u, v, w)$ represented by $\{A\}$ and $\{B\}$ are attached to the base and moving platforms, respectively. In FIG. 13, $s_i$ represents the unit vector along the axes of i-th rotary actuator and $d_i$ is the vector along $A_iB_i$ with the length of $d_i$. Assuming that each limb is connected to the fixed base by a universal joint, the orientation of i-th limb with respect to the fixed base can be described by two successive rotations, rotation $\theta_i$ around the axis $s_i$, followed by rotation $\psi_i$ around $n_i$, which is itself perpendicular to both $d_i$ and $s_i$. It is to be noted that $\theta_i$, and $d_i$ are active joints, actuated by the rotary and linear actuators, respectively, while, $\psi_i$ is an inactive joint.

In FIG. 13, $a_i$ which represents $OA_i$ can be written as $a_i = g[\cos \gamma_i \sin \gamma_i \ 0]^T$, where g and h are the radius of the fixed and moving platforms, respectively, $^Bb_i$ represents the position of the i-th joint on the platform in the moving frame $\{B\}$, $^Bb_i = PB_i)_B$. $^Bb_i$ is constant and is equal to $^Bb_i = a_i = h[\cos \gamma_i \sin \gamma_i \ 0]^T$. We can represent $$\frac{A}{B}R = [r_{i,j}],$$

the rotation matrix from A to B, using Euler angles as $$\frac{A}{B}R = \begin{bmatrix} c\alpha_2 c\alpha_3 & -c\alpha_2 s\alpha_3 & s\alpha_2 \\ c\alpha_3 s\alpha_2 s\alpha_1 + s\alpha_3 c\alpha_1 & -s\alpha_3 s\alpha_2 s\alpha_1 + c\alpha_3 c\alpha_1 & -c\alpha_2 s\alpha_1 \\ -c\alpha_3 s\alpha_2 c\alpha_1 + s\alpha_3 s\alpha_1 & s\alpha_3 s\alpha_2 c\alpha_1 + c\alpha_3 s\alpha_1 & c\alpha_2 c\alpha_1 \end{bmatrix}. \quad (1)$$

where $s\alpha_1 = \sin \alpha_1$ and $c\alpha_1 = \cos \alpha_1$, and so on. $\alpha_1$, $\alpha_2$, and $\alpha_3$ are three Euler angles defined according to the x-y-z convention. Thurs, the vector $^Bb_i$ would be expressed in the fixed frame $\{A\}$ as $$b_i = {}^A_B R P B_i)_B. \quad (2)$$

Let p and $r_i$ denote the position vectors for P and $B_i$ in the reference frame $\{A\}$, respectively. From the geometry, $$r_i = p + b_i. \quad (3)$$

Subtracting vector $a_i$ from both sides of (3) one obtains $$r_i - a_i = p + b_i - a_i. \quad (4)$$

Left hand side of (4) is the definition of $d_i$, therefore $$d_i^2 = (p + b_i - a_i) \cdot (p + b_i - a_i). \quad (5)$$

Using Euclidean norm $d_i$ can be expressed as $$d_i = \sqrt{((x-x_i)^2 + (y-y_i)^2 + (z-z_i)^2)}. \quad (6)$$

in which $$\begin{cases} x_i = -h(\cos \gamma_i \ r_{11} + \sin \gamma_i \ r_{21}) + g \cos \gamma_i \\ y_i = -h(\cos \gamma_i \ r_{12} + \sin \gamma_i \ r_{22}) + g \sin \gamma_i \\ z_i = -h(\cos \gamma_i \ r_{13} + \sin \gamma_i \ r_{23}) \end{cases} \quad (7)$$

Coordinates $C_i(A_i, x_i, y_i, z_i)$ are connected to the base platform with their $x_i$ axes aligned with the rotary actuators in the $s_i$ directions, with their $z_i$ axes perpendicular to the fixed platform. Thus, one can express vector $d_i$ in $\{C_i\}$ as $$^{c_i}d_i = d_i \begin{bmatrix} \sin \psi_i \\ -\sin \theta_i \cos \psi_i \\ \cos \theta_i \cos \psi_i \end{bmatrix}. \quad (8)$$

From the geometry, $$r_i = a_i + {}^A_{C_i}R \ {}^{C_i}d_i, \quad (9)$$

where $$\frac{A}{C_1}R$$

is the rotation matrix from $\{C_i\}$ to $\{A\}$, $$\frac{A}{C_i}R = \begin{bmatrix} \cos \gamma_i & -\sin \gamma_i & 0 \\ \sin \gamma_i & \cos \gamma_i & 0 \\ 0 & 0 & 1 \end{bmatrix}. \quad (10)$$

By equating the right sides of (3) and (4), and solving the resultant equation, $\psi_i$, and $\theta_i$ can be calculated as follows:

$$\psi_i = \sin^{-1}\left(\frac{\cos \gamma_i (x - x_i) + \sin \gamma_i (y - y_i)}{d_i}\right), \quad (11)$$

and $$\theta_i = \sin^{-1}\left(\frac{\sin \gamma_i (x - x_i) - \cos \gamma_i (y - y_i)}{d_i \cos \psi_i}\right). \quad (12)$$

The kinematic performance of the system has been compared to a known Gough-Stewart platform in terms of reachability. Consider the two mechanisms with g=1 (m) and h=0.5 (m), respectively; where g and h are the radii of the fixed and moving platforms, respectively. By assuming a cubic with 1 m length, 1 (m) width and 1 (m) height located 0.25 (m) above the base platform, we are interested in determining the volume percentage in which the mechanism can successfully reach the locations within this cubic space.

Figure 14:
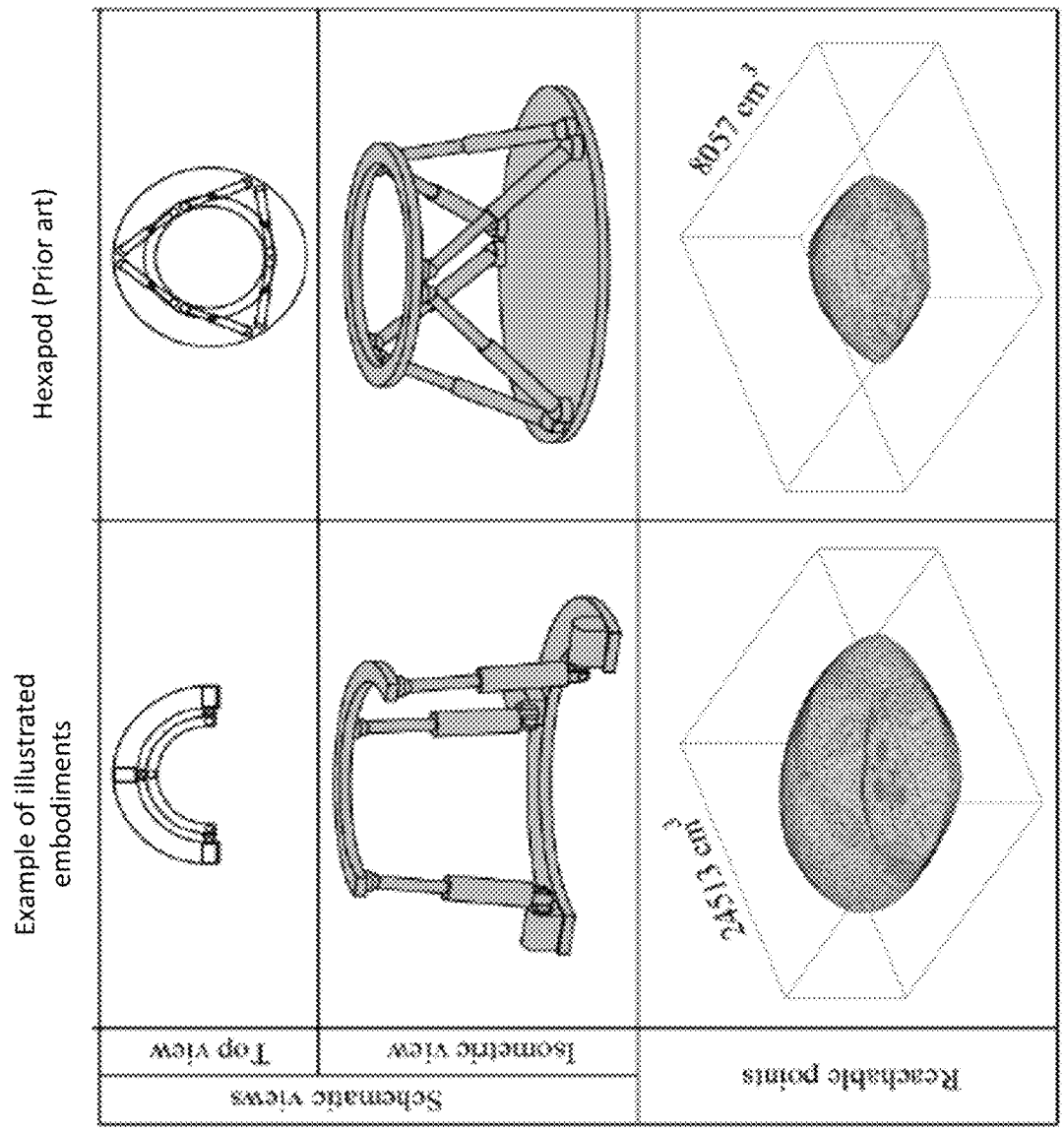
FIG. 14 shows a workspace analysis of some illustrated embodiments compared to the known Gough-Stewart platform.

As shown in FIG. 14, the reachable space in the Stewart platform is much smaller than that of the wide-open mechanism. This is due to the fact that, in the 6-legged Stewart-like UPS mechanisms, the workspace is constructed by intersection of six spheres. However, in the illustrated embodiments that have three leg structures, the workspace is constructed by intersection of only three spheres.

The performance of the robot was evaluated in an experimental study on a prototype of the illustrated embodiments. During the experiments, an optical stereoscopic vision system such as a system made by Claron Technology Inc., Ontario, Canada, was used as an external observer to track the robots end-effector, i.e., the center of the moving platform. In the illustrated system shown in FIG. 11, a 3D camera was used to detect a set of markers attached to the moving platform to find its position and orientation with respect to a fixed Cartesian coordinate system, defined using another set of markers attached to the frame.

In the experiments, at first, the workspace of an example of a robotic system was measured by running its actuators in different directions to the end of the moving range, and recording the end-effector position by the optical tracker. The results indicated a circular truncated workspace, which was sufficiently large for fracture reduction maneuvers in spite of the fact that the spherical joints used in the prototype could rotate only up to ±25 deg.

Figure 15:
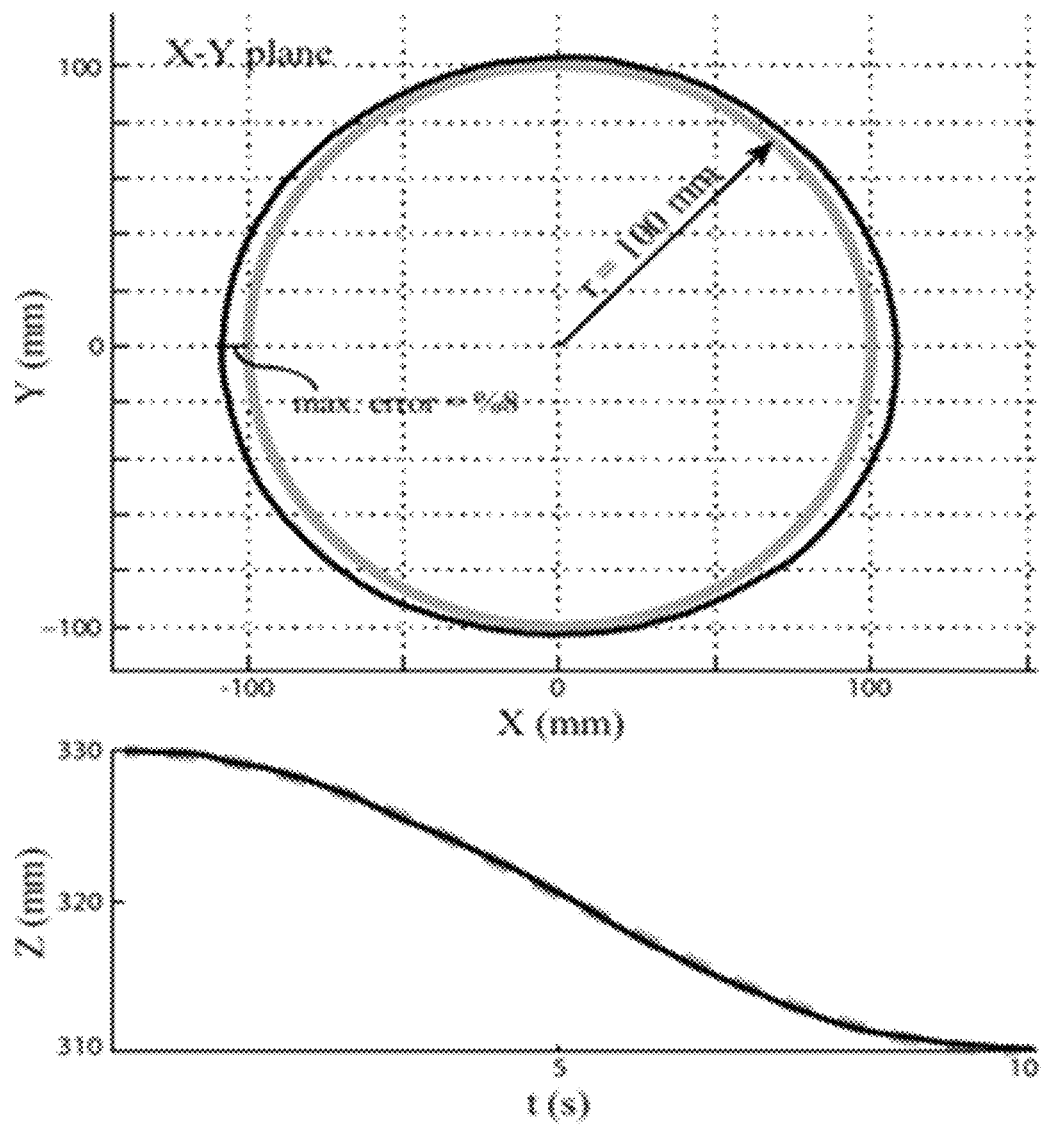
FIG. 15. shows experimental verification of robot movements according to some embodiments.

In the next stage, trajectory tracking experiments were performed to verify the robots kinematical model and assess the effects of the friction and backlash. As shown in FIG. 15 in each test, a desired trajectory, e.g., an offset circle, was defined for the end-effector to be followed and the corresponding joint trajectory for each actuator was computed, using the inverse kinematics equations, to generate the position data of the actuators. The top figure illustrates a planar circular motion. The maximum error is %8 in two spots, due to an existing joint clearance. The bottom figure illustrates the vertical movements. The robot follows the prescribed path. The experiments revealed reasonably acceptable results. The example robot that was used in the experiments, according to some embodiments, was capable of moving the end-effector on a 100 (mm) radius circle co-centered with a virtual point with a maximum deviation from the reference trajectory of about 8 mm.

Figure 16:
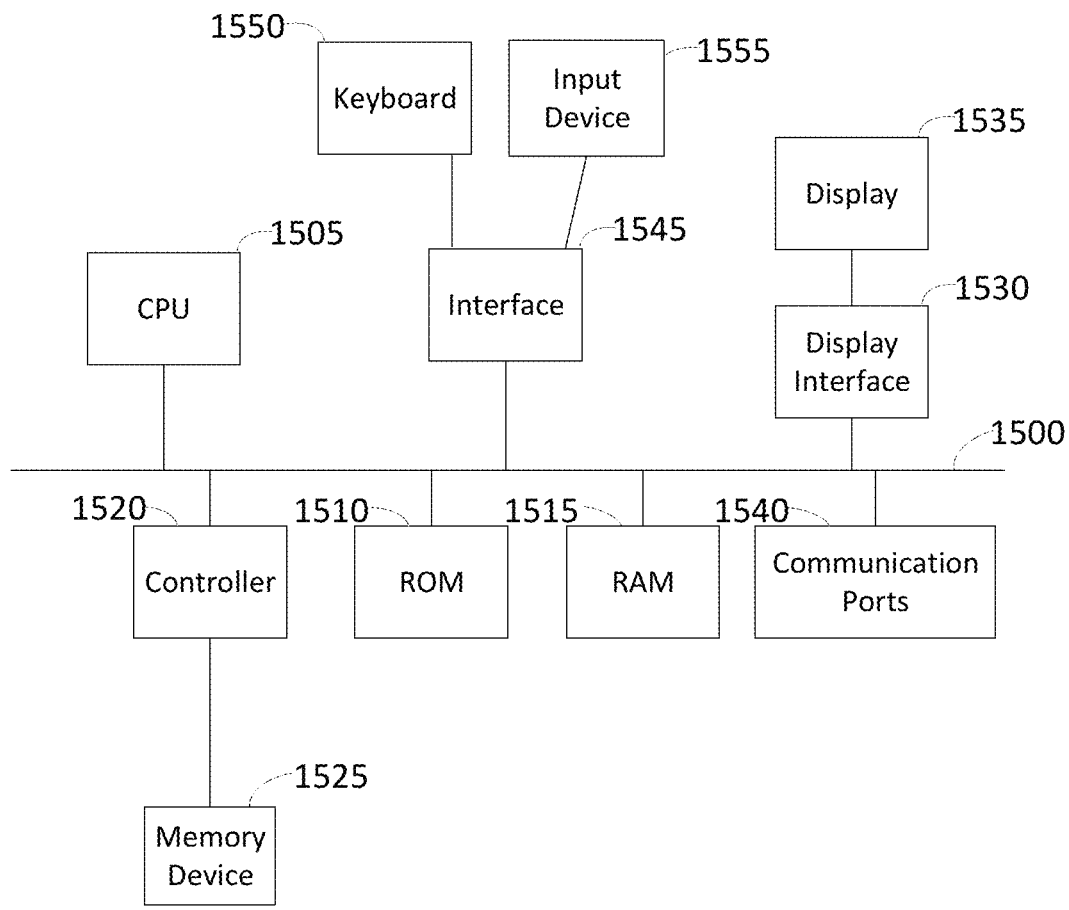
FIG. 16 depicts an example of internal hardware that may be included in any of the electronic components of the robotic system.

The above illustrated embodiments described in FIGS. 1-12 can be implemented in various configurations. For example, the system may implement the control functions by a processor installable on the robot, a processor of the robotic system or a processor on a cloud. FIG. 16 depicts an example of internal hardware that may be included in any of the electronic components of the system, such as the processing device, the robot, or the robotic system. An electrical bus 1500 serves as an information highway interconnecting the other illustrated components of the hardware. Processor 1505 is a central processing device of the system, configured to perform calculations and logic operations required to execute programming instructions. As used in this document and in the claims, the terms "processor" and "processing device" may refer to a single processor or any number of processors in a set of processors, whether a central processing unit (CPU) or a graphics processing unit (GPU) or a combination of the two. Read only memory (ROM) 1510, random access memory (RAM) 1515, flash memory, hard drives and other devices capable of storing electronic data constitute examples of memory devices 1525. A memory device, also referred to as a computer-readable medium, may include a single device or a collection of devices across which data and/or instructions are stored.

An optional display interface 1530 may permit information from the bus 1500 to be displayed on a display device 1535 in visual, graphic or alphanumeric format. An audio interface and audio output (such as a speaker) also may be provided. Communication with external devices may occur using various communication devices 1540 such as a transmitter and/or receiver, antenna, an RFID tag and/or short-range or near-field communication circuitry. A communication device 1540 may be attached to a communications network, such as the Internet, a local area network or a cellular telephone data network.

The hardware may also include a user interface sensor 1545 that allows for receipt of data from input devices 1550 such as a keyboard, a mouse, a joystick, a touchscreen display 1530, a remote control, a pointing device, a video input device and/or an audio input device. Digital image frames also may be received from an imaging capturing device 1555 such as an x-ray scanner to capture one or more images of the bone fractures during the reduction procedure.

Optionally, the hardware may not need to include a memory, but instead programming instructions are running on one or more virtual machines or one or more containers on a cloud. For example, the processing device may be a server on a cloud that includes multiple virtual machines, each virtual machine having an OS, a virtual disk, virtual network and Apps, and the programming instructions for implementing various functions in the print system may be stored on one or more of those virtual machines on the cloud.

Reduction is a crucial step in the surgical treatment of bone fractures to achieve anatomical alignment and facilitate healing. The illustrated embodiments provide a 6-degree-of-freedom wide-open parallel mechanism for computer assisted fracture reduction of long bones, and are advantageous over known Gough-Stewart platform. As a result, a larger workspace is achieved, sufficient for surgical maneuvers. The system could provide the fine adjustments easily as its force capacity was sufficiently higher than the counteracting forces and torques produced by rubber bands.

The moving frame of the system is lighter than the conventional counterpart as the rotary actuators are resting on the fixed platform, which allows for higher accelerations to be available due to the smaller inertial effects. Further, the legs of the mechanism are configured non-symmetrically on semicircles on the base and moving platforms, enabling the mechanism to embrace and manipulate column-shape objects such as long bones easily.

In some embodiments, the system may also be used clinically in order to improve the quality of fracture reduction with no need to repetitive manipulations, and reduce the amount of radiation exposure to the operating staff and patients. The initial configuration of the bone fragments can be found from the CT data and the desired target configuration from the morphological features of the bone, as well as the geometry of the fracture ends. An optimal path from the initial to the desired target configuration would enable a closed reduction procedure with improved accuracy and less soft tissue damage.

In one preferred embodiment, methods of performing a long bone surgery are describe using a surgical robot that provides 6-degrees-of-freedom to empower the surgical team. In some embodiments, the method employs the robot that includes a fixed frame defining a first plane, wherein the fixed frame includes an open space formed in a center region thereof; a moving frame defining a second plane, wherein the moving frame includes an open space in a center region thereof; three leg structures connecting the fixed frame and the moving frame, and configured to move the moving frame relative to the fixed frame; and a stabilizer configured to hold an anatomical structure in the open space formed in the center region of each of the moving frame and the fixed frame.

In at least another embodiment, the method may include attaching a proximal fragment of a fractured bone to a fixed frame of a robot, attaching a distal fragment of the fractured bone to a moving frame of the robot, moving the moving frame of the robot to stretch or align the distal fragment so that the distal fragment is positioned to the proximal fragment to maximize recovery time. The method may also include rotating the moving frame to cause the distal fragment subject to varus-valgus rotations so that a shaft of the distal fragment lies parallel to a shaft of the proximal fragment.

The presently described surgical methodologies may include treating complex fractures by translating the moving frame in a plane transverse to an axis of the proximal fragment to enable the axis of the distal fragment to align with an axis of the proximal fragment, and moving the moving frame to shorten the distal fragment to obtain a target pose for a fracture end of the distal fragment to align with an opposing fracture end of the proximal fragment.

In some embodiments, the steps of moving, rotating, translating and moving the moving frame may include using an ultrasonic or x-ray image capturing device to capture in real-time one or more, 2D or 3D images during the surgery, wherein the one or more captured images include the fracture end of the distal fragment and the opposing fracture end of the proximal fragment.

The various illustrated embodiments facilitate increased surgical workspace, while allowing precise alignment of fractured bones. Above-disclosed features and functions, as well as alternatives, may be combined into many other different systems or applications. Various components may be implemented in hardware or software or embedded software. Various presently unforeseen or unanticipated alternatives, modifications, variations or improvements may be made by those skilled in the art, each of which is also intended to be encompassed by the disclosed embodiments.

The invention claimed is:

1. A surgical robot comprising:
a fixed frame defining a first plane, wherein the fixed frame includes an open space formed in a center region thereof;
a moving frame defining a second plane, wherein the moving frame includes an open space formed in a center region thereof;
three leg structures connecting the fixed frame and the moving frame, and configured to move the moving frame relative to the fixed frame;
a stabilizer configured to hold an anatomical structure in the open space formed in the center region of each of the moving frame and the fixed frame;
wherein each of the three leg structures comprises a linear component that facilitates a sliding component to travel in a linear motion longitudinally along the leg structure, wherein the sliding component is coupled to the moving frame at a mounting location;
wherein the linear component of each leg structure is configured to be coupled to a first actuator to move the sliding component longitudinally along the leg structure; and
wherein the first actuator of each leg structure is a rotary actuator, and each leg structure further comprises a screw shaft configured to be coupled to the first actuator and to transfer rotational motion from the first actuator to the linear motion of the sliding component.

2. The robot of claim 1, wherein the stabilizer comprises:
at least one rod attached at varying locations along the fixed frame and extending from the fixed frame towards the open space formed in the center region thereof, wherein the at least one rod is configured to be positioned to hold a first fragment of the anatomical structure in place relative to the fixed frame; and
at least one rod attached at varying locations along the moving frame and extending from the moving frame towards the open space formed in the center region thereof, wherein the at least one rod is configured to be positioned to hold a second fragment of the anatomical structure in place relative to the moving frame.

3. The robot of claim 1, wherein each of the moving frame and the fixed frame are formed as a partially annular ring having an opening therein.

4. The robot of claim 1, wherein each leg structure further comprises: a rotary component mounted to the fixed frame at a mounting location; and
a connector connecting the linear component to the rotary component.

5. The robot of claim 4, wherein the connector is of a U-shape.

6. The robot of claim 4, wherein the rotary component comprises a shaft couplable to a shaft of a second rotary actuator and configured to transfer rotation of the second rotary actuator to the connector.

7. The robot of claim 6, wherein the rotary component further comprises a shaft connector positioned to be coupled to the shaft of the rotary component and also to pivotally connect to the connector of each leg structure.

8. The robot of claim 7, wherein the rotary component further comprises a key positioned to lock the shaft connector to the shaft of the rotary component.

9. The robot of claim 4, wherein:
the mounting locations at which the sliding components for the three leg structures are coupled to the moving frame are equally spaced; and
the mounting locations at which the rotary component for the three leg structures are mounted to the fixed frame are also equally spaced.

10. The robot of claim 4, wherein:
each of the moving frame and the fixed frame are formed as a partially annular ring having an opening therein;
the mounting location at which the sliding component for a middle leg structure of the three leg structures is coupled to the moving frame is adjustable along the partially annular ring of the moving frame; and the mounting location at which the rotary component for a middle leg structure of the three leg structures is mounted to the fixed frame is adjustable along the partially annular ring of the fixed frame.

11. The robot of claim 4, wherein the fixed frame comprises an extended plate at each mounting location, wherein each extended plate is configured to enable a rotary component to be mounted thereon, and further wherein each extended plate lies in the first plane.

12. The robot of claim 1, wherein the fixed frame is movably mounted to a stand that is configured to support the robot.

13. The robot of claim 12, wherein the robot further comprises an attachment device configured for attaching an image capturing device to the robot, wherein the image capturing device is capable of being positioned to capture one or more images in real-time during a surgery.

14. The robot of claim 13, wherein the image capturing device is selected from a group consisting of an ultrasound device and an x-ray scanner or a combination thereof.

15. The robot of claim 6, wherein the first and second rotary actuators for each leg structure is configured to rotate using a servo or stepper motor.

16. The robot of claim 1, further comprising:
a first additional element attachable to the fixed frame to close the opening of the fixed frame;
a second additional element attachable to the moving frame to close the opening of the moving frame; and
an additional leg structure comprising:
a linear component that is couplable to a first actuator to facilitate a sliding component to travel in a linear motion longitudinally along the additional leg structure, wherein the sliding component is mounted to the second additional element at a mounting location,
a screw shaft configured to be coupled to the first actuator and to transfer rotation of the first actuator to the linear motion of the sliding component,
a rotary component mounted to the first additional element, and
a connector connecting the linear component to the rotary component;
wherein the rotary component is a rotary gear box comprising:
a shaft couplable to a shaft of a second rotary actuator and configured to transfer rotation of the second rotary actuator to the connector, and
a shaft connector positioned to be coupled to the shaft of the rotary component and also pivotally connect to the connector of the additional leg structure.

17. The robot of claim 4, wherein the rotary component is a rotary gear box.

18. A robotic system for use in reduction procedure of long bone fractures or pelvic surgeries, comprising:
a robot according to claim 6;
a processing device in communication with the first and second rotary actuators of each leg structure; and
a non-transitory computer-readable storage medium containing programming instructions configured to cause the processing device to control each of the first and second actuators during the procedure.

19. The robotic system of claim 18, wherein:
each of the moving frame and the fixed frame are formed as a partially annular ring having an opening therein; and
the opening of the moving frame and the opening of the fixed frame are positionable around the long bone to reach a position for the procedure.

20. The robotic system of claim 18, wherein the fixed frame is movably mounted to a stand that is configured to support the robot and enable the robot to move freely to the position for the procedure.

21. The robotic system of claim 18, further comprising an image capturing device positioned to capture one or more images of the long bone fracture or pelvis in real-time during the procedure.

22. The robotic system of claim 21, wherein the image capturing device is selected from the group consisting of an ultrasound device, an x-ray scanner or a combination thereof.

* * * * *